(12) United States Patent
Zhang et al.

(10) Patent No.: US 8,796,285 B2
(45) Date of Patent: Aug. 5, 2014

(54) PYRAZOLO [1,5-A]-PYRIMIDONES DERIVATIVES AND PHARMACEUTICAL COMPOSITIONS AND USES THEREOF

(75) Inventors: Hailin Zhang, Shijiazhuang (CN); Jinlong Qi, Shijiazhuang (CN); Diqun Zhang, Shijiazhuang (CN); Kewei Wang, Beijing (CN); Fan Zhang, Shijiazhuang (CN); Yan Fu, Shijiazhuang (CN); Yi Mi, Shijiazhuang (CN); Wen Xu, Beijing (CN); Xiaona Du, Shijiazhuang (CN); Yibing Wu, Shijiazhuang (CN); Qingzhong Jia, Shijiazhuang (CN); Shuangge Yang, Shijiazhuang (CN)

(73) Assignees: Hebei Medical University, Shijiazhuang, Hebei (CN); Peking University, Beijing (CN)

( * ) Notice: Subject to any disclaimer, the term of this patent is extended or adjusted under 35 U.S.C. 154(b) by 20 days.

(21) Appl. No.: 13/377,138

(22) PCT Filed: Jun. 3, 2010

(86) PCT No.: PCT/CN2010/073531
§ 371 (c)(1),
(2), (4) Date: Dec. 8, 2011

(87) PCT Pub. No.: WO2010/142216
PCT Pub. Date: Dec. 16, 2010

(65) Prior Publication Data
US 2012/0088775 A1    Apr. 12, 2012

(30) Foreign Application Priority Data

Jun. 8, 2009 (CN) .......................... 2009 1 0074653

(51) Int. Cl.
*A01N 43/90* (2006.01)
*A61K 31/519* (2006.01)
*C07D 487/00* (2006.01)

(52) U.S. Cl.
USPC .................................... 514/259.31; 544/281

(58) Field of Classification Search
None
See application file for complete search history.

(56) References Cited

PUBLICATIONS

Checchi, et. al., Gazzetta Chimica Italiana (1955), 85, 1160-70.*
Mao, et. al., Bioorganic & Medicinal Chemistry Letters (2008), 18(19), 5320-5323.*

* cited by examiner

*Primary Examiner* — Jeffrey H Murray
(74) *Attorney, Agent, or Firm* — Raymond Y. Chan; David and Raymond Patent Firm

(57) ABSTRACT

The present invention provides new pyrazol-[1,5-a]-pyrimidone derivates and pharmaceutical compositions comprising said compounds and one or more pharmaceutically acceptable carriers or diluents. The uses of the compounds for the manufacture of potassium channel openers, anti-epilepsy medicaments, anti-anxiety medicaments and analgesic medicaments are also provided in the present invention.

3 Claims, 3 Drawing Sheets

PROCESS 1

PROCESS 2

PROCESS 3

PYRAZOLO [1,5-A]-PYRIMIDONES DERIVATIVES AND PHARMACEUTICAL COMPOSITIONS AND USES THEREOF

BACKGROUND OF THE PRESENT INVENTION

1. Field of Invention

The present invention relates to a compound and a pharmaceutical composition containing the compound and its medical use, and more particularly to pyrazolo-pyrimidones derivatives, their pharmaceutical compositions and application in opener of KCNQ potassium channel.

2. Description of Related Arts

KCNQ potassium channel is an important branch in family of potassium channel. At present, there are many different types of KCNQ potassium channels expressed in many different types of cells. According to their structural characteristics, 5 major types are categorized, which are KCNQ1, KCNQ2, KCNQ3, KCNQ4 and KCNQ5. Wherein KCNQ1 (also known as KVLQT) is mainly located in the heart and KCNQ2-5 are mainly located in the central and peripheral nervous systems, inner ear (KCNQ4), and muscle tissue (KCNQ5). Research studies have shown that both KCNQ1 and KCNE1 are coding for cardiac delayed rectifier potassium channel (IKs), and mutation of the channel can lead to hereditary long QT syndrome (LQT1, Sanguinetti M C, Ann N Y Acad. Sci. 1999; 868:406-13); KCNQ4 is gene coding for outer hair cell of ear and member of type-1 hair cell of vestibular organ which is associated with potassium channel, the mutation of which can lead to hereditary deafness; KCNQ2 and KCNQ3 channel genes co-express and generate current which is the molecular basis of neuronal M-type potassium current. M channel plays an important role in regulating the excitability of nerve cells and the genetic mutation of KCNQ2/Q3 will alter the function of M channel and may lead to nervous system diseases such as benign familial neonatal convulsions syndrome (BFNCs) (Maljevic S et al., J. Physiol. 2008 586(7):1791-801). KCNQ2/Q3 channel opener can reduce the neuronal excitability, thereby capable of treating diseases associated with neuronal over-excitability such as convulsions, epilepsy and neuropathic pain.

Patent EP554543 discloses a type of KCNQ opener Retigabine (D-23129; N-(2-amino-4-(4-fluorobenzylamino)-phenyl) carbamic acid ethyl ester). Retigabine has shown a promising anticonvulsant property in vivo and in vitro; is effective in reducing incidence of epilepsy (Bialer et al., Epilesy Research 2002, 52, 31-71). Neuropathic pain experiments based on animal model suggest that KCNQ channel opener can be used for pain disorder treatment (Blackburn-Munro et al., European Journal of Pharmacology 2003, 450, 109-116). In addition, the expression of KCNQ2-5 channel RNA in trigeminal ganglia, dorsal root ganglia and trigeminal caudate nucleus has implied that these channel openers may have an effect on feeling process of migraine (Goldstein et al., Society for Neuroscience Abstracts 2003, 53, 8). There is also report on Retigabine having activity on animal model of anxiety-like behavior (Korsgaard et al., J Pharmacol Exp Ther. 2005; 314(1): 282-92). Researchers also discovered the expression of mRNA of KCNQ2 and KCNQ3 subunits in hippocampus and amygdale which are associated with anxiety behavior and emotional behavior (such as bipolar disorder). It is suggested that KCNQ opener can be used for the treatment of neurological disorders such as anxiety disorder and bipolar disorder. Other researches further discover that KCNQ channel opener can effectively used for treatment of stroke (Jensen B S., CNS Drug Review 2002, 8(4):353-60), and also for treatment of diseases of excessive excitability in which the brain reward system is involved, such as cocaine abuse, nicotine withdrawal symptoms and alcohol withdrawal symptoms (Hansen et al., Eur J. Pharmacol. 2007; 570: 77/88).

In conclusion, KCNQ potassium channel not only involves in regulation of many important physiological functions in the body, but also has significant effect on certain diseases. Accordingly, more research and development of novel compounds for application as KCNQ potassium channel opener can provide more choices for clinical uses.

SUMMARY OF THE PRESENT INVENTION

An object of the present invention is to provide a novel compound of effective opener for KCNQ potassium channel, as well as a pharmaceutical composition containing the compound as the active ingredient, and a method of use of the compound and the pharmaceutical composition.

Additional advantages and features of the invention will become apparent from the description which follows, and may be realized by means of the instrumentalities and combinations particular point out in the appended claims.

According to the present invention, the foregoing and other objects and advantages are attained by providing a novel compound of effective opener for KCNQ potassium channel, which is a compound of pyrazolo-[1,5a]-pyrimidones derivatives having a general formula I as follows:

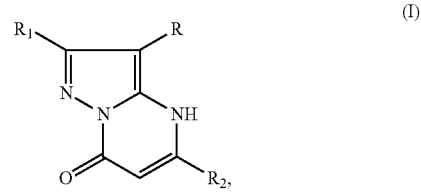

(I)

where:

R is alkyl, aryl, substituted aryl, heterocyclic compound, substituted heterocyclic compound or —COOR$_5$;

R$_1$ is hydrogen, halogen, alkyl, alkyl halide, aryl or substituted aryl;

R$_2$ is halogen, alkyl, substituted alkyl, aryl, substituted aryl, heterocyclic compound, substituted heterocyclic compound, or

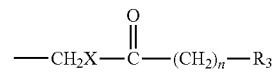

or —CH$_2$R$_4$;

X is O or NH, n is a natural number selected from 0 to 6,

R$_3$ is hydrogen, halogen, aryl or substituted aryl;

R$_4$ is fatty acid or cyclic imine; and

R$_5$ is an alkyl with 1-4 carbon.

Definition of Terminology:

Alkyl—refers to a branched or unbranched alkyl chain with 1-6 carbon atoms, which includes but not limited to: methyl, ethyl, prop-1-yl, prop-2-yl, 2-methyl-prop-1-yl, 2-methyl-prop-2-yl, but-1-yl, but-2-yl, 3-methyl-but-1-yl, 3-methyl-but-2-yl, pent-1-yl, pent-2-yl, pent-3-yl, hex-1-yl and hex-2-yl.

Substituted alkyl—refers to the alkyl as defined in the above having a process of substitution reaction in which one hydrogen is replaced with halogen or carboxyl. Examples are trifluoromethyl, trichloromethyl and methyl halide.

Aryl—refers to one- or two-ring aromatic compound of phenyl or napthyl.

Substituted aryl—refers to the aryl with one or more substituent which is described below. Examples are methoxyphenyl and halogenated phenyl.

Halogen—refers to fluorine, chlorine, bromine and iodine.

Alkyl halide—refers to the alkyl with flurine, chlorine, bromine or iodine substituent. It can be a mono-, di-, or tri-halogenated alkyl such as tri-halogenated methyl which includes trifluoromethyl and trichloromethyl.

Heterocyclic compound—refers to aromatic compound which contains N, O or S atom such as pyridine, pyrimidine, pyrazole, furan, indole, thiophene and etc.

Substituted aryl or substituted heterocyclic compound—refers to a compound with a primary ring having one or more substituents, such as 0, 1, 2, 3 or 4 substituents which replace the —H in the primary ring structure. The number of substituents can be one or more, and the substituent can be selected independently from the followings: halogen, mono-halogenated substituent, trichloro substituent, $C_{1-6}$ alkyloxy, halogenated $C_{1-6}$ alkyloxy, nitro, and sulfonyl amide.

According to the preferred embodiment of the present invention, $R_1$ is preferably an alkyl halide (halogenated alkyl). In particular, tri-halogenated alkyl is mostly preferred.

Preferably, the carbon chain consists of 1-4 carbon atoms in straight-chain or branched-chain.

"The compound" of the present invention refers to any one of the illustrative or exemplary embodiments having the general formula I and described in the present invention.

According to a first exemplary embodiment of the preferred embodiment of the present invention, the compound of the present invention is: a compound having a general formula I, where R is a methyl acetate substituent, $R_1$ is a halogenated alkyl, and $R_2$ is a phenyl or a substituted phenyl.

According to a second exemplary embodiment of the preferred embodiment of the present invention, the compound of the present invention is: a compound having a general formula I, where R is a phenyl or a substituted phenyl, $R_1$ is a halogenated alkyl, and $R_2$ is a phenyl or a substituted phenyl.

According to a third exemplary embodiment of the preferred embodiment of the present invention, the compound of the present invention is: a compound having a general formula I, where R is a naphthalenyl or a substituted naphthalenyl, $R_1$ is a halogenated alkyl, and $R_2$ is a phenyl or a substituted phenyl.

According to a fourth exemplary embodiment of the preferred embodiment of the present invention, the compound of the present invention is: a compound having a general formula I, where R is a thiophenyl, $R_1$ is a halogenated alkyl, and $R_2$ is a phenyl or a substituted phenyl.

According to a fifth exemplary embodiment of the preferred embodiment of the present invention, the compound of the present invention is: a compound having a general formula I, where R is a thiophenyl, $R_1$ is a halogenated alkyl, and $R_2$ is an alkyl or a substituted alkyl.

According to a sixth exemplary embodiment of the preferred embodiment of the present invention, the compound of the present invention is: a compound having a general formula I, where R is a naphthalenyl or a substituted naphthalenyl, $R_1$ is a tri-halogenated alkyl, and $R_2$ is a phenyl or a substituted phenyl.

According to a seventh exemplary embodiment of the preferred embodiment of the present invention, the compound of the present invention is: a compound having a general formula I, where R is a thiophenyl, $R_1$ is a halogenated alkyl, and $R_2$ is a

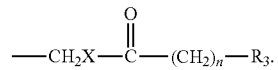

According to an eighth exemplary embodiment of the preferred embodiment of the present invention, the compound of the present invention is: a compound having a general formula I, where R is a thiophenyl, $R_1$ is a halogenated alkyl, and $R_2$ is a pyridine or a substituted pyridine.

According to the above description, the inventors of the present invention further provide 120 exemplary examples to illustrate the compound having a general formula I in an explicit manner (which is illustrated in Table 1), so as to provide description in relation to the general formula I and the substituents in further details. However, the compound of the present invention is not limited to the exemplary examples in Table 1.

TABLE 1

| Compound No. | Nomenclature |
|---|---|
| 1 | ethyl 7-oxo-5-phenyl-2-(trifluoromethyl)-4,7-dihydropyrazolo[1,5-a]pyrimidine-3-carboxylate |
| 2 | 3-(3,4-dimethoxyphenyl)-2,5-bis(trifluoromethyl)pyrazolo[1,5-a]pyrimidin-7(4H)-one |
| 3 | ethyl 7-oxo-2-(trifluoromethyl)-5-chloromethyl-4,7-dihydropyrazolo[1,5-a]pyrimidine-3-carboxylate |
| 4 | ethyl 7-oxo-5-methyl-2-(trifluoromethyl)-4,7-dihydropyrazolo[1,5-a]pyrimidine-3-carboxylate |
| 5 | methyl 7-oxo-5-phenyl-2-(trifluoromethyl)-4,7-dihydropyrazolo[1,5-a]pyrimidine-3-carboxylate |
| 6 | ethyl 7-oxo-2-(trifluoromethyl)-5-(2,6-dichloro-5-fluoropyridine)-4,7-dihydropyrazolo[1,5a]pyrimidine-3-carboxylate |
| 7 | ethyl 7-oxo-5-(Piperidin-1-ylmethyl)-2-(trifluoromethyl)-4,7-dihydropyrazolo[1,5-a]pyrimidine-3-carboxylate |
| 8 | 2-trifluoromethyl-3-(4-fluorophenyl)-5-(4-chlorophenyl)-pyrazole[1,5-a]pyrimidin-7(4H)-one |
| 9 | ethyl 7-oxo-5-(piperazin-1-yl)-2-(trifluoromethyl)-4,7-dihydropyrazolo[1,5a]pyrimidine-3-carboxylate |
| 10 | ethyl 7-oxo-5-(2,3,4,5-tetrafluorophenyl)-2-(trifluoromethyl)-4,7-dihydropyrazolo[1,5a]pyrimidine-3-carboxylate |
| 11 | ethyl 7-oxo-5-(4-methoxyphenyl)-2-(trifluoromethyl)-4,7-dihydropyrazolo[1,5a]pyrimidine-3-carboxylate |

TABLE 1-continued

| Compound No. | Nomenclature |
|---|---|
| 12 | ethyl 7-oxo-5-(2-nitrophenyl)-2-(trifluoromethyl)-4,7-dihydropyrazolo[1,5-a]pyrimidine-3-carboxylate |
| 13 | ethyl 7-oxo-5-(tert-butyl)-2-(trifluoromethyl)-4,7-dihydropyrazolo[1,5-a]pyrimidine-3-carboxylate |
| 14 | ethyl 7-oxo-5-(3,4,5-trimethoxyphenyl)-2-(trifluoromethyl)-4,7-dihydropyrazolo[1,5a]pyrimidine-3-carboxylate |
| 15 | ethyl 7-oxo-5-(2,4,5-trifluorophenyl)-2-(trifluoromethyl)-4,7-dihydropyrazolo[1,5a]pyrimidine-3-carboxylate |
| 16 | ethyl 7-oxo-5-isopropyl-2-(trifluoromethyl)-4,7-dihydropyrazolo[1,5a]pyrimidine-3-carboxylate |
| 17 | N-((3-(3,4-dimethoxyphenyl)-7-oxo-2-(trifluoromethyl)-dihydropyrazolo[1,5-a]pyrimidin-5-yl)methyl)-2-(4-trifluoromethyl)phenyl)acetamide |
| 18 | 5-(2,6-dichloro-5-fluoropyrindin-3-yl)-3-(4-fluorophenyl)-2-(trifluoromethyl)pyrazolo[1,5-a]pyrimidin-7(4H)-one |
| 19 | 3,5-diphenyl-2-(trifluoromethyl)pyrazolo[1,5-a]pyrimidin-7(4H)-one |
| 20 | 2,5 bis(trifluoromethyl)-3-phenylpyrazolo [1,5-a]pyrimidin-7(4H)-one |
| 21 | 5-chloromethyl-3-phenyl-2-trifluoromethylpyrazolo[1,5-a]pyrimidin-7(4H)-one |
| 22 | 5-(2,6-dichloro-5-fluoropyrimidin-3-yl)-3-(4-fluorophenyl)-2-(trifluoromethyl))pyrazolo [1,5-a]pyrimidin-7(4H)-one |
| 23 | 5-(2,6-dichloro-5-fluoropyrimidine)-3-(3,4-dimethoxyphenyl)-2-trifluoromethyl pyrazolo [1,5-a]pyrimidin-7(4H)-one |
| 24 | 5-(2,6-dichloro-5-fluoropyrimidin-3-yl)-3-phenyl-2-trifluoromethylpyrazolo [1,5-a]pyrimidin-7(4H)-one |
| 25 | 5-(piperidin-1-ylmethyl)-3-phenyl-2-trifluoromethylpyrazolo[1,5-a]pyrimidin-7(4H)-one |
| 26 | 5-(4-chlorophenyl)-3-phenyl-2-trifluoromethylpyrazolo[1,5-a]pyrimidin-7(4H)-one |
| 27 | 5-(piperazin-1-yl)-3-phenyl-2-(trifluoromethyl)pyrazolo [1,5-a]pyrimidin-7(4H)-one |
| 28 | 3-phenyl-5-(2,3,4,5-tetrafluorophenyl)-2-(trifluoromethyl)pyrazolo[1,5-a]pyrimidin-7(4H)-one |
| 29 | 5-(4-methoxyphenyl)-3-phenyl-2-trifluoromethylpyrazolo[1,5-a]pyrimidin-7(4H)-one |
| 30 | 5-(3-nitrophenyl)-3-phenyl-2-trifluoromethylpyrazolo[1,5-a]pyrimidin-7(4H)-one |
| 31 | 3-phenyl-5-tert-butyl-2-trifluoromethylpyrazolo[1,5-a]pyrimidin-7(4H)-one |
| 32 | 3-phenyl-2-trifluoromethyl-5-(3,4,5-trimethyloxyphenyl)pyrazole [1,5-a]pyrimidin-7(4H)-one |
| 33 | 3-phenyl-2-trifluoromethyl-5-(2,4,5-trifluorophenyl)pyrazolo[1,5-a]pyrimidin-7(4H)-one |
| 34 | 5-isopropyl-3-phenyl-2-trifluoromethylpyrazolo[1,5-a]pyrimidin-7(4H)-one |
| 35 | N7-oxo-3-phenyl-2-(trifluoromethyl)-4,7-dihydropyrazolo[1,5-a]pyrimidin-5-yl)methyl)-2-(4-trifluoromethylphenyl)-acetamide |
| 36 | 7-oxo-3-phenyl-2-(-trifluoromethyl)-4,7-dihydropyrazolo[1,5-a]pyrimidin-5-yl)methyl 2-(4-(trifluoromethyl)phenyl)acetate |
| 37 | 3-(naphthalen-1-yl)-5-pheny-2-trifluoromethylpyrazolo[1,5-a]pyrimidin-7(4H)-one |
| 38 | 2,5-bis(trifluoromethyl)-3-(naphthalen-1-yl)pyrazolo[1,5-a]pyrimidin-7(4H)-one |
| 39 | 5-chloromethyl-3-(naphthalen-1-yl)-2-trifluoromethylpyrazolo[1,5-a]pyrimidin-7(4H)-one |
| 40 | 5-methyl-3-(naphthalen-1-yl)-2-trifluoromethylpyrazolo[1,5-a]pyrimidin-7(4H)-one |
| 41 | 3-(naphthalen-1-yl)-5-phenyl-2-trifluoromethylpyrazolo[1,5-a]pyrimidin-7(4H)-one |
| 42 | 5-(2,6-dichloro-5-fluoropyrimidine)-3-(naphthalen-1-yl)-2-trifluoromethyl pyrazolo[1,5-a]pyrimidin-7(4H)-one |
| 43 | 3-(naphthalen-1-yl)-5-(piperidin-1-yl methyl)-2-trifluoromethylpyrazolo[1,5-a]pyrimidin-7(4H)-one |
| 44 | 5-(4-chlorophenyl)-3-(naphthalen-1-yl)-2-trifluoromethylpyrazolo[1,5-a]pyrimidin-7(4H)-one |
| 45 | 3-(naphthalen-1-yl)-5-(piperidin-1-yl)-2-trifluoromethylpyrazolo[1,5-a]pyrimidin-7(4H)-one |
| 46 | 3-(naphthalen-1-yl)-5-(2,3,4,5-tetrafluorophenyl)-2-trifluoromethylpyrazolo[1,5-a]pyrimidin-7(4H)-one |
| 47 | 5-(4-methoxyphenyl)-3-(naphthalen-1-yl)-2-trifluoromethylpyrazolo[1,5-a]pyrimidin-7(4H)-one |
| 48 | 3-(naphthalen-1-yl)-5-(3-nitrophenyl)-2-trifluoromethylpyrazolo[1,5-a]pyrimidin-7(4H)-one |
| 49 | 3-(naphthalen-1-yl)-5-tert-butyl-2-trifluoromethylpyrazolo[1,5-a]pyrimidin-7(4H)-one |
| 50 | 3-(naphthalen-1-yl)-2-trifluoromethyl-5-(3,4,5-trimethoxyphenyl)pyrazolo[1,5-a]pyrimidin-7(4H)-one |

TABLE 1-continued

| Compound No. | Nomenclature |
|---|---|
| 51 | 3-(naphthalen-1-yl)-2-trifluoromethyl-5-(2,4,5-trifluorophenyl)pyrazolo[1,5-a]pyrimidin-7(4H)-one |
| 52 | 5-isopropyl-3-(naphthalen-1-yl)-2-trifluoromethylpyrazolo[1,5-a]pyrimidin-7(4H)-one |
| 53 | N-((2-trifluoromethyl-3-(naphthalen-1-yl)-7-oxo-4,7-dihydro pyrazole[1,5-a]pyrimidin-5-yl)methyl)-2-(4-trifluoromethylphenyl)-acetamide |
| 54 | 3-(naphthalen-1-yl)-7-oxo-2-(trifluoromethyl)-4,7-dihydropyrazolo[1,5-a]pyrimidin-5-yl)methyl 2-(4-(trifluoromethyl)phenyl)acetate |
| 55 | 5-phenyl-3-(thiophen-2-yl)-2-trifluoromethylpyrazolo[1,5-a]pyrimidin-7(4H)-one |
| 56 | 3-(thiophen-2-yl)-2,5-(trifluoromethyl)pyrazolo[1,5-a]pyrimidin-7(4H)-one |
| 57 | 2-chloro-5-chloromethyl-3-(thiophen-2-yl)-pyrazolo[1,5-a]pyrimidin-7(4H)-one |
| 58 | 5-methyl-3-(thiophen-2-yl)-2-trifluoromethylpyrazolo[1,5-a]pyrimidin-7(4H)-one |
| 59 | 5-phenyl-3-(thiophen-2-yl)-2-trichloromethylpyrazolo[1,5-a]pyrimidin-7(4H)-one |
| 60 | 5-(2,6-dichloro-5-fluoropyrimidine)-3-(thiophen-2-yl)-2-trifluoromethyl pyrazolo[1,5-a]pyrimidin-7(4H)-one |
| 61 | 5-(piperidin-1-ylmethyl)-3-(thiophen-2-yl)-2-trifluoromethylpyrazolo[1,5-a]pyrimidin-7(4H)-one |
| 62 | 5-(4-chlorophenyl)-3-(thiophen-2-yl)-2-trifluoromethylpyrazolo[1,5-a]pyrimidin-7(4H)-one |
| 63 | 5-(piperidin-l-ylmethyl)-3-(thiophen-2-yl)-2-trifluoromethylpyrazolo[1,5-a]pyrimidin-7(4H)-one |
| 64 | 5-(2,3,4,5-tetrafluorophenyl)-3-(thiophen-2-yl)-2-trifluoromethylpyrazolo[1,5-a]pyrimidin-7(4H)-one |
| 65 | 5-(4-methoxyphenyl)-3-(thiophen-2-yl)-2-trifluoromethylpyrazolo[1,5-a]pyrimidin-7(4H)-one |
| 66 | 5-(3-nitrophenyl)-3-(thiophen-2-yl)-2-trifluoromethylpyrazolo[1,5-a]pyrimidin-7(4H)-one |
| 67 | 5-tert-butyl-3-(thiophen-2-yl)-2-trifluoromethylpyrazolo[1,5-a]pyrimidin-7(4H)-one |
| 68 | 3-(thiophen-2-yl)-2-trifluoromethyl-5-(3,4,5-trimethoxyphenyl)pyrazolo[1,5-a]pyrimidin-7(4H)-one |
| 69 | 3-(thiophen-2-yl)-2-trifluoromethyl-5-(2,4,5-trifluorophenyl)pyrazolo[1,5-a]pyrimidin-7(4H)-one |
| 70 | 5-isopropyl-3-(thiophen-2-yl)-2-trifluoromethylpyrazolo[1,5-a]pyrimidin-7(4H)-one |
| 71 | N-((2-trifluoromethyl-3-(thiophen-2-yl)-7-oxo-4,7-dihydropyrazolo[1,5-a]pyrimidin-5-yl)methyl)-2-(4-trifluoromethylphenyl)-acetamide |
| 72 | (7-oxo-3-(thiophen-2-yl)-2-(trifluoromethyl)-4,7-dihydropyrazolo[1,5-a]pyrimidin-5-yl)methyl 2-((4-(trifluoromethyl)phenyl)acetate |
| 73 | ethyl 7-oxo-2-(4-chlorophenyl)-5-(trifluoromethyl)-4,7-dihydropyrazolo[1,5-a]pyrimidine-3-carboxylate |
| 74 | 2-(4-chlorophenyl)-3-phenyl-5-trifluoromethylpyrazolo[1,5-a]pyrimidin-7(4H)-one |
| 75 | 2-(4-chlorophenyl)-3-(naphthalen-2-yl)-5-trifluoromethylpyrazolo[1,5-a]pyrimidin-7(4H)-one |
| 76 | 2-(4-chlorophenyl)-3-(thiophen-2-yl)-5-trifluoromethylpyrazolo[1,5-a]pyrimidin-7(4H)-one |
| 77 | 2-(4-chlorophenyl)-3-(1H-indol-3-yl)-5-trifluoromethylpyrazolo[1,5-a]pyrimidin-7(4H)-one |
| 78 | ethyl 2-(4-chlorophenyl)-5-chloromethyl-7-oxo-4,7-dihydropyrazolo[1,5-a]pyrimidine-3-carboxylate |
| 79 | 5-chloromethyl-2-(4-chlorophenyl)-3-phenylpyrazolo[1,5-a]pyrimidin-7(4H)-one |
| 80 | 5-chloromethyl-2-(4-chlorophenyl)-3-(naphthalen-2-yl)-pyrazolo[1,5-a]pyrimidin-7(4H)-one |
| 81 | 5-chloromethyl-2-(4-chlorophenyl)-3-(thiophen-2-yl)-pyrazolo[1,5-a]pyrimidin-7(4H)-one |
| 82 | 5-chloromethyl-2-(4-chlorophenyl)-3-(1H-indol-3-yl)-pyrazolo[1,5-a]pyrimidin-7(4H)-one |
| 83 | ethyl 7-oxo-5-(3-fluorophenyl)-2-(4-chlorophenyl)-4,7-dihydropyrazolo[1,5-a]pyrimidine-3-carboxylate |
| 84 | (2-(4-chlorophenyl)-7-oxo-3-phenyl-4,7-dihydropyrazolo[1,5-a]pyrimidin-5-yl)methyl-2,2,2trifluoroacetate |
| 85 | (2-trifluoromethyl-7-oxo-3-phenyl-4,7-dihydropyrazolo[1,5-a]pyrimidin-5-yl)methyl-2,2,2-trifluoroacetate |
| 86 | (2-trifluoromethyl-3-piperazinyl-7-oxo-4,7-dihydropyrazolo[1,5-a]pyrimidin-5-yl)methyl-2,2,2-trifluoroacetate |
| 87 | (2-trifluoromethyl-3-(4-fluorophenyl)-7-oxo-4,7-dihydropyrazolo[1,5-a]pyrimidin-5-yl)methyl-2,2,2-trifluoroacetate |

TABLE 1-continued

| Compound No. | Nomenclature |
|---|---|
| 88 | (2-trifluoromethyl-3-(thiophen-2-yl)-7-oxo-4,7-dihydropyrazolo[1,5-a]pyrimidin-5-yl)methyl-2,2,2-trifluoroacetate |
| 89 | (2-(4-chlorophenyl)-3-(thiophen-2-yl)-7-oxo-4,7-dihydropyrazolo[1,5-a]pyrimidin-5-yl)methyl-2,2,2-trifluoroacetate |
| 90 | 5-(2,6-dichloro-5-fluoropyrimidine)-2-(4-chlorophenyl)-3-(thiophen-2-yl)-pyrazolo[1,5-a]pyrimidin-7(4H)-one |
| 91 | 2-(4-chlorophenyl)-5-(2,6-dichloro-5-fluoropyrido)-3-phenyl pyrazolo[1,5-a]pyrimidin-7(4H)-one |
| 92 | 2-(4-chlorophenyl)-5-(2,6-dichloro-5-fluoropyrido)-3-(naphthalen-1-yl)-pyrazolo[1,5-a]pyrimidin-7(4H)-one |
| 93 | 5-(2,6-dichloro-5-fluoropyrido)-3-(naphthalen-1-yl)-3-trichloromethyl pyrazolo[1,5-a]pyrimidin-7(4H)-one |
| 94 | 5-(2,6-dichloro-5-fluoropyrido)-3-(thiophen-2-yl)-2-trichloromethyl pyrazolo[1,5-a]pyrimidin-7(4H)-one |
| 95 | N-((2-trichloromethyl-3-(thiophen-2-yl)-7-oxo-4,7-dihydro pyrazolo[1,5-a]pyrimidin-5-yl)methyl)-2-(4-trifluoromethylphenyl)-acetamide |
| 96 | 5-chloromethyl-3-(thiophen-2-yl)-2-trifluoromethylpyrazolo[1,5-a]pyrimidin-7(4H)-one |
| 97 | 3-(thiophen-2-yl)-2-trichloromethyl-5-trifluoromethylpyrazolo[1,5-a]pyrimidin-7(4H)-one |
| 98 | 3-(thiophen-2-yl)-2-trichloromethyl-5-(2,4,5-trifluorophenyl)pyrazolo[1,5-a]pyrimidin-7(4H)-one |
| 99 | 3-phenyl-2-trichloromethyl-5-(2,4,5-trifluorophenyl)pyrazolo[1,5-a]pyrimidin-7(4H)-one |
| 100 | 5-(4-methoxyphenyl)-3-phenyl-2-trichloromethylpyrazolo[1,5-a]pyrimidin-7(4H)-one |
| 101 | 2-(4-chlorophenyl)-3-phenyl-5-(4-methoxyphenyl)pyrazolo[1,5-a]pyrimidin-7(4H)-one |
| 102 | 2-(4-chlorophenyl)-3-phenyl-5-isopropylpyrazolo[1,5-a]pyrimidin-7(4H)-one |
| 103 | 3-(thiophen-2-yl)-5-(2,6-dichloro-5-fluoropyrimidine)pyrazolo[1,5-a]pyrimidin-7(4H)-one |
| 104 | ethyl 7-oxo-5-(piperidin-1-yl-methyl)-4,7-dihydropyrazolo[1,5a]pyrimidine-3-carboxylate |
| 105 | 3-phenyl-5-(piperidin-1-yl)pyrazolo[1,5-a]pyrimidin-7(4H)-one |
| 106 | N-((2-methyl-3-(thiophen-2-yl)-7-oxo-4,7-dihydropyrazolo[1,5-a]pyrimidin-5-yl)methyl)-2-(4-trifluoromethylphenyl)-acetamide |
| 107 | 2-methyl-3-(thiophen-2-yl)-5-chloromethylpyrazolo[1,5-a]pyrimidin-7(4H)-one |
| 108 | 2-chloro-3-(thiophen-2-yl)-5-chloromethylpyrazolo[1,5-a]pyrimidin-7(4H)-one |
| 109 | 2-chloro-3-phenyl-5-chloromethylpyrazolo[1,5-a]pyrimidin-7(4H)-one |
| 110 | 2-chloro-3-(naphthalen-1-yl)-5-chloromethylpyrazolo[1,5-a]pyrimidin-7(4H)-one |
| 111 | 2-chloro-3-phenyl-5-(piperidin-1-yl)pyrazolo[1,5-a]pyrimidin-7(4H)-one |
| 112 | 2-chloro-3-phenyl-5-trifluoromethylpyrazolo[1,5-a]pyrimidin-7(4H)-one |
| 113 | N-((2-chloro-3-(thiophen-2-yl)-7-oxo-4,7-dihydropyrazolo[1,5-a]pyrimidin-5-yl)methyl)-2-(4-trifluoromethylphenyl)-acetamide |
| 114 | 2-chloro-3-(thiophen-2-yl)-5-(3-nitrophenyl)pyrazolo[1,5-a]pyrimidin-7(4H)-one |
| 115 | (2-chloro-3-phenyl-7-oxy-4,7-dihydro pyrazole[1,5-a]pyrimidin-5-yl)methyl acetate |
| 116 | N-((2-chloro-3-(naphthalen-2-yl)-7-oxo-4,7-dihydropyrazolo[1,5-a]pyrimidin-5-yl)methyl)-2,2,2-trifluoroacetamide |
| 117 | (2-chloro-3-phenyl-7-oxo-4,7-dihydropyrazolo[1,5-a]pyrimidin-5-yl)methyl-2,2,2-trifluoroacetate |
| 118 | N-((2-trifluoromethyl-3-phenyl-7-oxo-4,7-dihydro pyrazolo[1,5-a]pyrimidin-5-yl)-2-phenyl)acetamide |
| 119 | 2-chloro-3-methyl-5-isopropylpyrazolo[1,5-a]pyrimidin-7(4H)-one |
| 120 | 2-chloro-3-methyl-5-(3,4,5-trimethoxy)pyrazolo[1,5-a]pyrimidin-7(4H)-one |

In particular, the preferred embodiments are the compound of the present invention as follows:
2-trifluoromethyl-3-phenyl-5-chloromethylpyrazolo[1,5-a]pyramindin-7(4H)-one;
2-trifluoromethyl-3-phenyl-5-(2,6-dichloro-5-fluoropyrimidine)pyrazolo[1,5-a]pyrimidin-7(4H)-one;
2-trifluoromethyl-3-(naphthalen-1-yl)-5-chloromethylpyrazolo[1,5]pyrimidin-7(4H)-one;
3-(naphthalen-1-yl)-2,5-bis(trifluoromethyl)-pyrazolo[1,5]pyrimidin-7(4H)-one;
2-trifluoromethyl-3-phenyl-5-(piperidin-1-ylmethyl)pyrazolo[1,5-a]pyrimidin-7(4H)-one.

The compound of the present invention can be in the form of a free base or a salt form. In free base application, physically acceptable substances of inorganic acid (such as hydrochloric acid, sulfuric acid, hydrobromic acid, hydroiodic acid and phosphoric acid), organic acid (such as acetic acid, propanoic acid, citric acid, maleic acid, malic acid, tartaric acid and methanesulformic acid) can be used to form the salt form.

A second object of the present invention is to provide a pharmaceutical composition which contains the compound of the present invention serving as an active ingredient as well as one or more pharmaceutically acceptable carrier or diluting agent.

The pharmaceutically acceptable carrier or diluting agent of the present invention refers to the excipient, additive or solvent which are commonly used in the pharmaceutical preparation. For examples, lactose, sucrose, dextrin, talc powder, gelatin, agar, pectin, gum arabic, magnesium stearate, stearic acid, lower alkyl ethers of cellulose, corn starch, potato starch, gum, syrup, peanut oil, olive oil, phospholipids, fatty acid, fatty amine, glyceryl monostearate, glyceryl distearate, coloring agent, flavoring agent, preservative, water, ethanol, propanol, saline solution, glucose solution and etc.

The compound and the pharmaceutical composition are prepared into KCNQ potassium opener, and can be prepared into a pharmaceutical agent in different forms for combating epilepsy;

prepared into a pharmaceutical agent in different forms for combating anxiety;

prepared into a pharmaceutical agent in different forms for analgesia.

The specific preparation process can be carried out under routine condition. For example, the compound of the present invention can be used as the active ingredient to process with water, sucrose, sorbitol, fructose and etc. for forming an oral agent; or to process with an excipient such as lactose, glucose, sucrose, mannitol and etc., a disintegrant such as starch and etc., a lubricant such as stearic acid, talc and etc., and a binding agent such as gelatin and polyvinyl alcohol for forming a tablet or capsule; or to process with saline, glucose solution or a mixing agent of saline and glucose solution for forming an injection agent. Or to prepare into sterile powder for injection and a variety of releasing agents, suspension agents, emulsion agents and etc.

According to the preferred embodiment of the present invention, the pharmaceutical agent for combating epilepsy can be used for prevention, suppression, mitigation or treatment of convulsion and seizure, continuous seizure and epilepsy symptoms.

According to the preferred embodiment of the present invention, the pharmaceutical agent for combating anxiety can be used for prevention, suppression, mitigation or treatment of anxiety disorder caused or induced by various causes. For example, panic disorder of different causes, obsessive-compulsive disorder, anxiety disorder caused by medical conditions, substance-induced anxiety disorder, separation anxiety disorder, adjustment disorder, behavioral anxiety, hypochondria and etc.

According to the preferred embodiment of the present invention, the pharmaceutical agent for analgesia can be used for prevention, suppression, mitigation or treatment of neuropathic pain of different kinds and migraine.

The compound of the present invention which is prepared into the pharmaceutical agents can be applied through oral administration or non-oral administration. Dosage can be adjusted based on the form of the pharmaceutical agent, frequency of administration, method of administration, medical history, patient's physical conditions and health conditions. In general, the daily dosage of 50-500 mg is generally preferred. Practitioner can adjust the dosage according to clinical observations.

The compound of the present invention, through toxicology testing, does not show significant toxic effect on human's body.

Still further objects and advantages will become apparent from a consideration of the ensuing description and drawings.

These and other objectives, features, and advantages of the present invention will become apparent from the following detailed description, the accompanying drawings, and the appended claims.

DETAILED DESCRIPTION OF THE PREFERRED EMBODIMENT

A preparation process of the compound of the present invention

The compound of the present invention can be prepared through general routine methods.

The present invention provides a preparation process which is specific to the compound of the present invention, which is a process as illustrated below (for details, refer to FIG. 1 and FIG. 2 or FIG. 1 and FIG. 3). In the process, the meanings of R, $R_1$, $R_2$ is the same as the meaning in the general formula I.

(1) Synthesis of intermediates of the compound of the present invention (such as the compound shown in the general formula (e)):

Add sodium metal into anhydrous alcohol to form a dissolved solution after sodium is dissolved; add the compound with the general formula (a) and (b) into the dissolved solution while the dissolved solution is hot; carry out reflux reaction for forming a prepared substance, which is then reacted with hydrazine sulfate and dimethyl carbonate to form the pyrazole derivative having the general formula (e). The process is shown in details in FIG. 1.

The pyrazole derivative having the general formula (e) which is prepared in the above process is an important intermediate of the compound of the present invention.

(2) Synthesis of target compound:

Add the pyrazole derivative having the general formula (e) into the compound having a general formula (f); Allow reflux reaction for four hours in which acetic acid is used as the solvent; and obtain the target compound having the general formula (I).

(3) Synthesis of target compound: Add the pyrazole derivative having the general formula (e) into halogenated ethyl acetoacetate (such as 4-Chloro Ethyl Acetoacetate), allow reflux reaction for four hours in acetic acid, obtain the target compound having the general formula (i), then use the target compound having the general formula (i) as the raw materials to carry out three reaction routes.

Route 1: the compound having the general formula (i) is used to obtain the compound having the general formula (j) by Gabriel reaction, then react with a corresponding acid under catalytic effect of EDC and DMAP to obtain a compound having the general formula (m);

Route 2: the compound having the general formula (i) is directly used to react with a corresponding imino compound to obtain a compound having the general formula (I);

Route 3: the compound having the general formula (i) is used to obtain the compound having the general formula (k) by affinity and substitution reactions, then react with a corresponding acid under catalytic effect of EDC and DMAP and obtain a compound having the general formula (n) by condensation reaction.

The general formula (i), (j), (m), (l), (k) and (n) are particular formula of the general formula I of the compound of the present invention, which are used to further describe the compound of the present invention.

Figure 1:
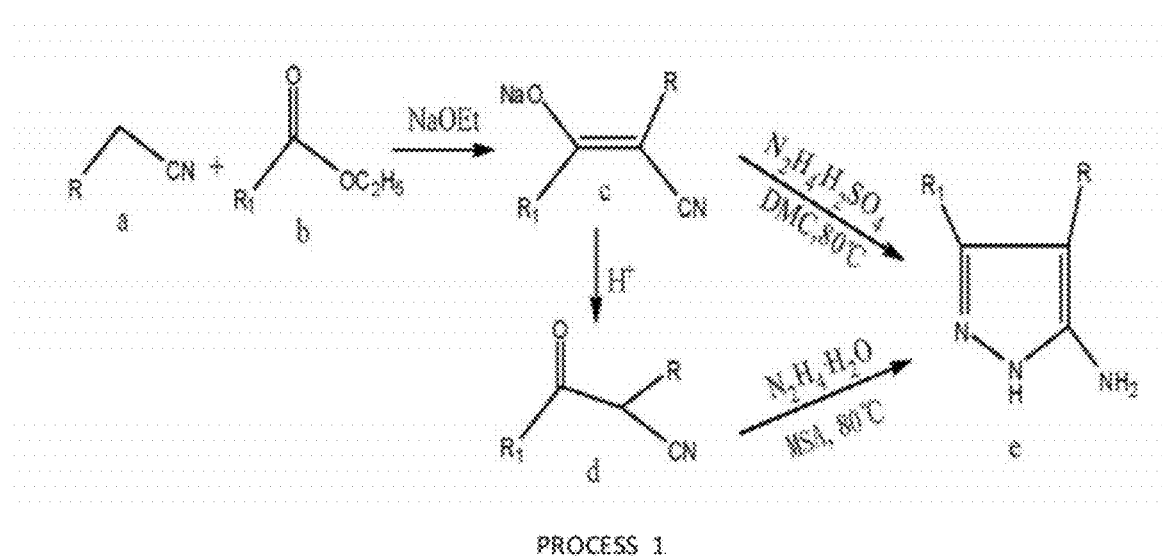
FIG. 1 illustrates a process with intermediate compounds according to the preferred embodiment of the present invention.
Figure 3:
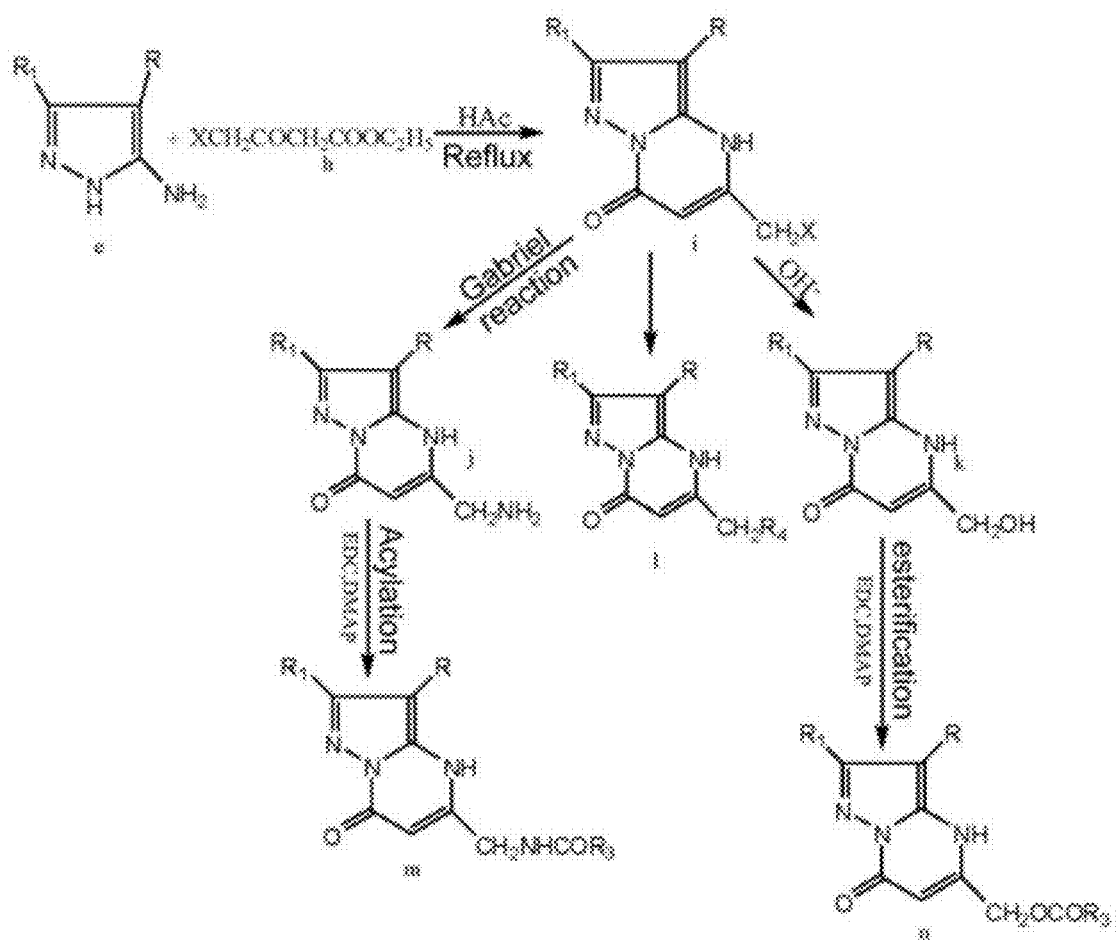

Referring to FIG. 1 and FIG. 3 of the drawings, the process can be used to synthesize the compound of the present invention having the general formula I in which $R_2$ is halogen, alkyl, substituted alkyl, aryl, substituted aryl, heterocyclic compound, substituted heterocyclic compound,

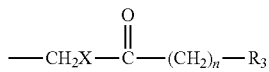

or —$CH_2R_4$.

In the above process, all the reagents can be obtained through commercial sales channel.

DETAILED DESCRIPTION OF THE EMBODIMENTS OF THE PRESENT INVENTION

The following exemplary embodiments 1-8 are the specific synthetic examples of the important intermediates and the compound of the present invention.

Exemplary Embodiment 1

(1) Synthesis of intermediate "4-phenyl-3-trifluoromethyl-5-amino-1H-pyrazole"

Referring to the process as shown in FIG. 1 of the drawings, add 2.3 g of sodium into 25 ml absolute ethanol (anhydrous alcohol) to form a dissolved solution; after completely dissolved, add phenyl acetonitrile (11.7 g) and ethyl trifluoro acetate (15.8 g) when the dissolved solution is hot; allow reflux reaction for 2 hours; recover ethanol by reducing pressure to obtain a product; add 20 ml water to dissolve the product; wash with petroleum ether layer for three times with 15 ml for each time, evaporate the water layer and obtain 14.0 g white solid substance. Provide 4.75 g (20 mmol) of the solid substance, 5.2 g of hydrazine sulfate and 50 ml of dimethyl carbonate to react for 12 hours at 80° C., vacuum filtration, remove a filtrate of dimethyl carbonate, add 10 ml of isopropyl ether, allow re-crystallization, obtain 3.8 g of 4-phenyl-3-trifluoromethyl-5-amino-1H-pyrazole (which is an important intermediate of the compound of the present invention). The white solid has a purity which is greater than 98% (HPLC-UV by area normalization); ESI-Ms(m/z): 228.1 $(M+1)^+$.

(2) Synthesis of intermediate "4-(4-chlorophenyl)-3-trifluoromethyl-5-amino-1H-pyrazole"

Referring to the process as shown in FIG. 1 of the drawings, add 2.3 g of sodium into 25 ml absolute ethanol to form a dissolved solution; after completely dissolved, add (4-chlorophenyl)acetonitrile (15.1 g) and ethyl trifluoroacetate (15.8 g) when the dissolved solution is hot; allow reflux reaction for 2 hours; recover ethanol by reducing pressure to obtain a product; add 20 ml water to dissolve the product; wash with petroleum ether layer for three times with 15 ml for each time, adjust pH to 5-6 with diluted sulfuric acid for the water layer, extract with ethyl acetate for three times with 20 ml for each time, add suitable amount of anhydrous magnesium sulfate to dry the ester layer, evaporate and obtain 16.0 solid substance. Provide 4.95 g (20 mmol) of the solid substance, 2.0 g of hydrazine hydrate, 30 ml of anhydrous ethanol and 1.93 g of methyl methanesulfonate for reflux reaction for 0.5 hour, recover ethanol and obtain a concentrated substance, wash with water until the pH is stable, add 10 ml of isopropyl ether, allow re-crystallization, obtain 5.0 g of 4-(4-chlorophenyl)-3-trifluoromethyl-5-amino-1H-pyrazole. The white solid has a purity which is greater than 97% (HPLC-UV by area normalization); ES1-Ms(m/z): 262 $(M+1)^+$.

The following intermediate compounds are also important intermediates of the compound of the present invention, which can be synthesized through the process of FIG. 1 of the drawings. The particular operation can be refer to the embodiment 1 and adjusted appropriately based on the different properties of the particular compound using the general routine method.

3-chloro-4-phenyl-5-amino-1H-pyrazole:

A white solid having a purity which is greater than 98% (HPLC-UV by area normalization); ESI-Ms(m/z): 194 $(M+1)^+$.

4-(thiophen-2-yl)-3-chloro-5-amino-1H-pyrimidine:

A reddish brown solid having a purity which is greater than 97% (HPLC-UV by area normalization); ESI-Ms(m/z): 200 $(M+1)^+$.

4-(naphthen-1-yl)-3-trifluoromethyl-5-amino-1H-pyrazole:

A pale yellow solid having a purity which is greater than 95% (HPLC-UV by area normalization); ESI-Ms(m/z): 278.1 $(M+1)^+$.

Exemplary Embodiment 2

Synthesis of 5-chloromethyl-3-phenyl-2-trifluoromethylpyrazolo[1,5-a]pyrimidin-7(4H)-one (Hereafter Called Compound Number 21)

Figure 2:
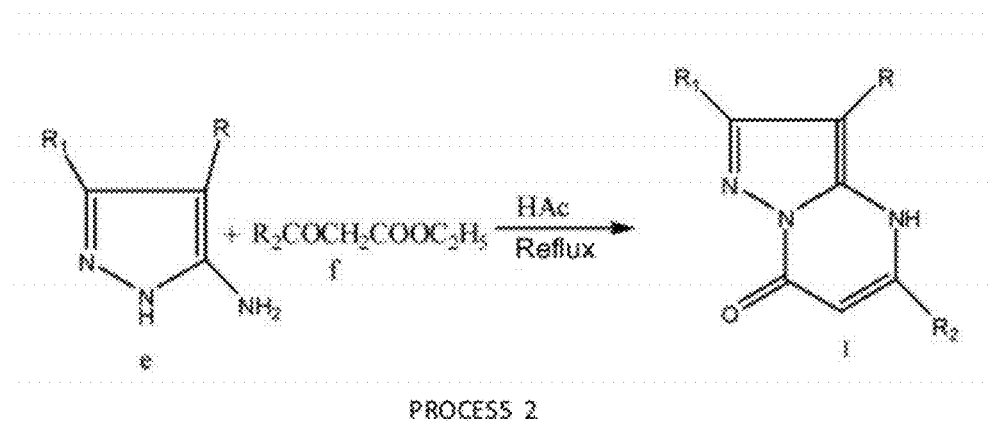
FIG. 2 and FIG. 3 illustrate a preparation process of the compound according to the above preferred embodiment of the present invention.

Referring to the process as shown in FIG. 2 of the drawings, provide and place 0.227 g of the intermediate 4-phenyl-3-trifluoromethyl-5-amino-1H-pyrazole (1 mmol), 0.130 g of ethyl 4-chloro-3-oxobutanoate and 3 ml of acetic acid (anhydrous acetic acid) into a parallel synthesis instrument (Buchi, Switzerland), allow reflux reaction for 4 hours, stop heating, filling cold water into the low temperature module of the synthesis instrument for precipitation of solid substance, wash with acetic acid, then wash with water until the solid substance is neutral, obtain 30 mg of 5-chloromethyl-3-phenyl-2-trifluoromethylpyrazolo[1,5-a]pyrimidin-7(4H)-one, which is a white solid. The purity is greater than 98% (HPLC-UV by area normalization); ESI-Ms(m/z): 328 $(M+1)^+$; $^1$HNMR (500 MHz, CD3OD): 7.56 (d, 2H), 7.42 (m, 2H), 7.33 (m, 1H), 6.12 (s, 1H), 4.57 (s, 2H).

Exemplary Embodiment 3

Synthesis of 2-trifluoromethyl-3-phenyl-5-(2,6-dichloro-5-fluoropyrindin-3-yl)pyrazolo[1,5-a]pyrimidin-7(4H)-one (Hereafter Called Compound Number 24)

(1) refer to the exemplary embodiment 1 for the synthesis of the intermediate 3-trifluoromethyl-4-phenyl-5-amino-1H-pyrazole.

(2) synthesis of compound number 24.

Obtain 0.227 g of 4-phenyl-3-trifluoromethyl-5-amino-1H-pyrazole (1 mmol) by referring to the process as shown in FIG. 2, 0.28 g of ethyl 3-(2,6-dichloro-5-fluoropyridin-3-yl)-3-oxopropanoate and 3 ml of anhydrous acetic acid. Place them into a parallel synthesis instrument (Buchi, Switzerland), allow reflux reaction for 4 hours, stop heating, filling cold water into the low temperature module of the synthesis instrument for precipitation of solid substance, wash with anhydrous acetic acid, then wash with water until the solid substance is neutral. The product is a neutral white solid having a yield of 30% and a purity greater than 97% (HPLC-UV by area normalization); ESI-Ms(m/z): 443 (M+1)+, $^1$HNMR (500 MHz, CD3OD): 7.54 (d, 2H), 7.41 (m, 2H), 7.33 (m, 1H), 6.12 (s, 1H).

Exemplary Embodiment 4

Synthesis of 5-chloromethyl-3-(naphthalen-1-yl)-2-trifluoromethylpyrazolo[1,5-a]pyrimidin-7(4H)-one (Hereafter Called Compound Number 39)

(1) Refer to the exemplary embodiment 1 for the synthesis of the intermediate 3-trifluoromethyl-4-(naphthalen-1-yl)-5-amino-1H-pyrazole.

(2) Synthesis of 5-chloromethyl-3-(naphthalen-1-yl)-2-trifluoromethyl pyrazolo[1,5-a]pyrimidin-7(4H)-one.

Obtain 0.277 g of 3-trifluoromethyl-4-(naphthalen-1-yl)-5-amino-1H-pyrazole (1 mmol) by referring to the process as shown in FIG. 2, 0.130 g of 4-chloro-acetoacetate and 3 ml of anhydrous acetic acid. Place them into a parallel synthesis instrument (Buchi, Switzerland), allow reflux reaction for 4 hours, stop heating, filling cold water into the low temperature module of the synthesis instrument for precipitation of solid substance, wash with anhydrous acetic acid, then wash with water until the solid substance is neutral, obtain the target product. The product is a white solid having a yield of 20% and a purity greater than 99% (HPLC-UV by area normalization); ESI-Ms(m/z): 378 (M+1)+, $^1$HNMR (500 MHz, CD3OD): 8.03 (d, 1H), 7.98 (d, 1H), 7.60 (q, 1H), 7.53 (m, 3H), 7.47 (m, 1H), 6.14 (s, 1H), 4.46 (s, 2H).

Exemplary Embodiment 5

Synthesis of 3-(naphthalen-1-yl)-2,5-bis(trifluoromethyl)-pyrazolo[1,5-a]pyrimidin-7(4H)-one (Hereafter Called Compound Number 38)

(1) Refer to the exemplary embodiment 1 for the synthesis of the intermediate 4-naphthalen-1-yl-3-trifluoromethyl-5-amino-1H-pyrazole.

(2) Synthesis of the compound number 38.

Obtain 0.277 g of 3-trifluoromethyl-4-(naphthalen-1-yl)-5-amino-1H-pyrazole (1 mmol) by referring to the process as shown in FIG. 2, 0.184 g of 3-fluoro-acetoacetate and 3 ml of anhydrous acetic acid. Place them into a parallel synthesis instrument (Buchi, Switzerland), allow reflux reaction for 4 hours, stop heating, filling cold water into the low temperature module of the synthesis instrument for precipitation of solid substance, wash with anhydrous acetic acid, then wash with water until the solid substance is neutral, obtain the compound number 38. The product (compound number 38) is a white solid having a yield of 5% and a purity greater than 99% (HPLC-UV by area normalization); ESI-Ms(m/z): 398 (M+1)+, $^1$HNMR (500 MHz, CD3OD): 8.03 (d, 1H), 7.98 (d, 1H), 7.60 (q, 1H), 7.53 (m, 3H), 7.47 (m, 1H), 6.44 (m, 1H).

Exemplary Embodiment 6

Synthesis of 5-(2,6-dichloro-5-fluoropyridin-3-yl)-3-(naphthalen-1-yl)-2-trifluoromethylpyrazolo[1,5-a]pyrimidin-7(4H)-one (Hereafter Called Compound Number 42)

(1) Refer to the exemplary embodiment 1 for the synthesis of the intermediate 4-naphthalen-1-yl-3-trifluoromethyl-5-amino-1H-pyrazole.

(2) Synthesis of the compound number 42.

Obtain 0.277 g of the intermediate 4-phenyl-3-trifluoromethyl-5-amino-1H-pyrazole (1 mmol) by referring to the process as shown in FIG. 2, 0.28 g of ethyl 3-(2,6-dichloro-5-fluoropyridin-3-yl)-3-oxopropanoate and 3 ml of anhydrous acetic acid. Place them into a parallel synthesis instrument (Buchi, Switzerland), allow reflux reaction for 4 hours, stop heating, filling cold water into the low temperature module of the synthesis instrument for precipitation of solid substance, wash with anhydrous acetic acid, then wash with water until the solid substance is neutral, obtain the compound number 42. The product (compound number 42) is a white solid having a yield of 35% and a purity greater than 99% (HPLC-UV by area normalization); ESI-Ms(m/z): 493 (M+1)+, $^1$HNMR (500 MHz, CD3OD): 8.00 (q, 2H), 7.96 (d, 1H), 7.59 (q, 1H), 7.53 (m, 3H), 7.41 (m, 1H), 6.12 (s, 1H).

Exemplary Embodiment 7

Synthesis of 2-trifluoromethyl-3-phenyl-5-(piperidin-1-yl methyl)pyrazolo[1,5-a]pyrimidin-7(4H)-one (Hereafter Called Compound Number 25)

Put 0.327 g of the compound number 21, 0.3 g of K2CO3 and 0.22 g of piperazine into 10 ml of DMF, heat to 50° C., allow reaction at the temperature for 1 hour, cool until room temperature is met, add 20 ml of water, after cooling, extract with ethyl acetate for two times with 15 ml for each time, wash the ester layer with suitable amount of water, evaporate ethyl acetate, and precipitate out 218 mg of the target compound 25. The product (compound number 25) is a white solid having a purity greater than 99.8% (HPLC-UV by area normalization); ESI-Ms(m/z): 377.15 (M+1)+, $^1$HNMR (500 MHz, CD3OD): 7.55 (q, 2H), 7.42 (m, 2H), 7.33 (m, 1H), 5.83 (s, 1H), 4.10 (s, 2H), 3.30 (m, 4H), 1.82 (m, 4H), 1.66 (t, 3H).

Exemplary Embodiment 8

Synthesis of N4(7-oxo-3-phenyl-2-(trifluoromethyl)-4,7-dihydropyrazolo[1,5-a]pyrimidin-5-yl)methyl)-2-(4-(trifluoromethyl)phenyl)acetamide (Hereafter Called Compound Number 35)

(1) Preparation of 5-aminomethyl-3-phenyl-2-trifluoromethylpyrazolo[1,5-a]pyrimidin-7(4H)-one Add 0.3 g of potassium phthalimide salt into a three-necked flask, then add 20 ml of anhydrous DMF and 0.327 g of the compound 21, allow reaction at 100° C. for 8 hours, cool until room temperature, add 20 ml of water and then extract with ethyl acetate for three times with 15 ml for each time, wash the ester layer with 20 ml of water, and dry with anhydrous magnesium sulfate. Evaporate to obtain a 0.50 g white solid. Pour the entire white solid obtained into 20 ml anhydrous ethanol, dissolve completely and then add 0.2 ml hydrazine hydrate (80%), allow reflux reaction for half hour. Recover ethanol, and obtain a white solid for re-crystallization with suitable concentration of diluted alcohol, obtain 0.18 g of 5-aminomethyl-3-phenyl-2-trifluoromethylpyrazolo[1,5-a]pyrimidin-7(4H)-one.

(2) Synthesis of Target Compound

Obtain 0.154 g of the above 5-aminomethyl-3-phenyl-2-trifluoromethyl pyrazolo[1,5-a]pyrimidin-7(4H)-one by referring to the process as shown in FIG. 3, 0.192 g of EDC HCl, 0.15 g of DMAP and 0.1 g of 4-(trifluoromethyl)phenylacetic acid, dissolve in 20 ml of dichloromethane, allow overnight reaction at room temperature. The dichloromethane is washed with 5% hydrochloric acid for three times with 15 ml for each time, then wash with 5% sodium bicarbonate for three times with 15 ml for each time, and then wash with 20 ml of water for one time to recover trifluoromethyl phenylacetic acid. Obtain a white solid which is 0.2 g, allow re-crystallization with small amount of 70% ethanol and obtain 0.08 g of the compound number 35. The product (compound number 35) is a white solid having a purity greater than 99% (HPLC-UV by area normalization); ESI-Ms(m/z): 495.15 (M+1)$^+$, $^1$HNMR (500 MHz, CD3OD): 7.82 (d, 2H), 7.54 (m, 2H), 7.46 (m, 4H), 7.38 (m, 1H), 5.89 (s, 1H), 4.04 (s, 2H), 3.55 (s, 2H).

Referring to the method illustrated in the exemplary embodiment 1 to 8 and standard chemical synthesis, the compound of the present invention can be prepared with suitable selection of reactants and reaction conditions. For example, the followings can be prepared:

3,5-diphenyl-2-trifluoromethylpyrazolo[1,5-a]pyrimidin-7(4H)-one (Compound Number 19):

A white solid with a yield of 50% and a purity greater than 99.5% (HPLC-UV by area normalization); ESI-Ms(m/z): 356.09 (M+1)$^+$, $^1$HNMR (500 MHz, CD3OD): 7.67 (d, 1H), 7.54 (m, 1H), 7.46 (t, 1H), 7.38 (m, 6H), 7.31 (d, 2H).

methyl 7-oxo-5-phenyl-2-(trifluoromethyl)-4,7-dihydropyrazolo[1,5-a]pyrimidine-3-carboxylate (Compound Number 5):

A white solid with a yield of 18% and a purity greater than 97% (HPLC-UV by area normalization); ESI-Ms(m/z): 352.08 (M+1)$^+$, $^1$HNMR (500 MHz, CD3OD): 8.05 (m, 2H), 7.53 (m, 2H), 7.41 (m, 1H), 7.38 (m, 6H), 5.98 (s, H), 4.36 (q, 4H), 1.35 (t, 3H).

2-chloro-5-chloromethyl-3-(thiophen-2-yl)-pyrazolo[1,5-a]pyrimidin-7(4H)-one (Compound Number 108):

A white solid with a yield of 38% and a purity greater than 98% (HPLC-UV by area normalization); ESI-Ms(m/z): 299.8 (M+1)$^+$, $^1$HNMR (500 MHz, CD3OD): 7.4 (m, 1H), 7.17 (m, 3H), 7.67 (m, 1H), 6.12 (s, 1H), 4.46 (s, 2H).

The compound of the present invention has shown physiological or pharmaceutical active effect in at least one of the following testing:

Exemplary example 9: High throughput by Atomic absorption of Rb$^+$ efflux testing (1) Testing compound: compound number 24 and 42.

(2) Testing method:

Atomic absorption Rb$^+$ efflux testing is a fast and safe selection method for high throughput potassium channel moderator, and is characterized in that the activity of the ion channel and the control effect of the opener are directly reflected. Rb and K have similar atomic size, and potassium ion channel is permeable to Rb$^+$. By testing concentration of the Rb$^+$ efflux, a status of the potassium channel, which is an open status or a close status, can be determined. Rb has specific absorption at 780 nm, and Rb$^+$ concentration can be determined by atomic absorption spectroscopy. Accordingly, analysis method of atomic absorption spectroscopy can be used to select the opener/inhibitor of potassium channel through high throughput of Rb$^+$ efflux.

Stable cell transfer of CHO cell of KCNQ4 channel at log phase and inoculate in 96-well culture plate at a density of 2×10$^4$ unit/well. Each concentration has a triplicate-hole setting, and a control setting with solvent of corresponding concentration. Allow growth against the well-wall overnight, then discard the culture medium, add 200 μl loading buffer which contains RbCl, and culture in 5% CO$_2$ at 37° C. for 3 hours. Then remove the loading buffer and wash with wash buffer for 3 times. Screen for the KCNQ opener, dilute testing compound with depolarization buffer, add 200 μl of the above solvent into the cell and allow reaction for 10 minutes. Incubate for 10 minutes, then carefully draw 200 μl supernatant to another 96-well culture plate, use ICR8000 atomic absorption spectrometry to determine the Rb$^+$ atomic absorption at 780 nm. Based on the equation Fsupern=(Rb_supern/cpd/Rb_supern/d)×100, calculate the corresponding rate of efflux.

Figure 4:
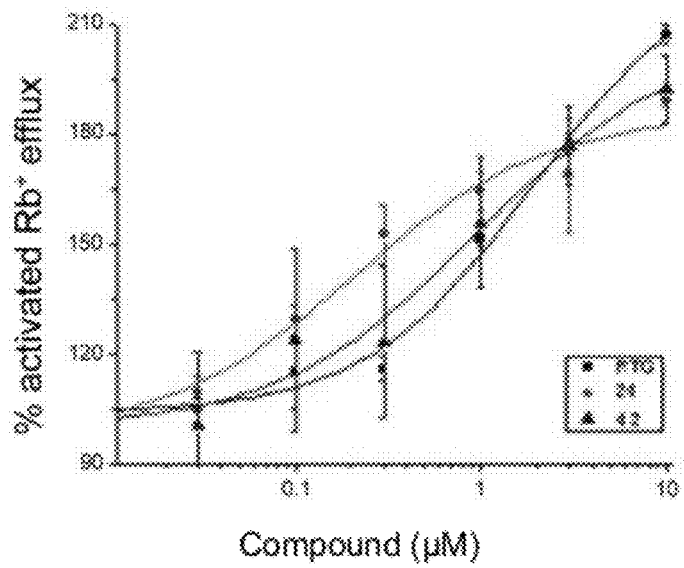
FIG. 4 is a spectrum of the compound analyzed by atomic absorption and $Rb^+$ efflux according to the above preferred embodiment of the present invention.

(3) Testing Result:

Referring to FIG. 4 of the drawings, the compound number 24 and 42 are tested by using atomic absorption of Rb+ efflux in high throughput testing at concentration of 0.03, 0.1, 0.6, 1, 3 and 10 μM respectively and the results show that both the compound number 24 and 42 have a dose-dependent activating effect on the CHO cell of the KCNQ4 potassium ion channel. RTG (which is Retigabine) is an experimental positive control. In the testing group of compound number 24, EC$_{50}$=0.21±0.08 μM; in the testing group of compound number 42, EC$_{50}$=0.96±0.51 μM.

Accordingly, the compound number 24 and 42 can be used as KCNQ4 potassium ion channel opener.

The above method is used to test the Rb$^+$ efflux of other compounds of the present invention and the testing results as illustrated in Table 2.

TABLE 2

| Compound Number | KCNQ2/3 (μM) | KCNQ4 (μM) | Purity (%) | m/z M + 1 |
|---|---|---|---|---|
| 2 | 5.65 ± 3.13 | 12.12 ± 0.23 | 99 | 408.1 |
| 5 | 100.2 ± 13.32 | 67.78 ± 2.67 | 97 | 352.1 |
| 8 | 4.76 ± 1.35 | 24.54 ± 4.67 | 95 | 408.1 |
| 18 | 78.65 ± 12.34 | 120.3 ± 3.23 | 93 | 491.1 |
| 19 | 40.23 ± 2.34 | 62.12 ± 1.12 | 99.5 | 356.1 |
| 20 | 1.28 ± 1.16 | 5.87 ± 2.67 | 97.9 | 348.1 |
| 21 | 3.61 ± 6.02 | 23.92 ± 0.43 | 98.2 | 328.1 |
| 22 | 1.28 ± 0.12 | 0.15 ± 0.09 | 98 | 461.1 |
| 23 | 22.12 ± 1.23 | 10.34 ± 0.43 | 96 | 503 |
| 24 | 0.078 ± 0.02 | 0.21 ± 0.08 | 97 | 443 |
| 25 | 85.31 ± 3.45 | 35.01 ± 1.21 | 99.8 | 377.1 |
| 30 | 1.26 ± 0.68 | 12.21 ± 0.82 | 97.5 | 401.8 |
| 35 | 138.11 ± 9.28 | 44.45 ± 5.28 | 99 | 495.1 |
| 38 | 9.29 ± 26.26 | 4.82 ± 3.45 | 99.2 | 398.1 |
| 39 | 5.21 ± 3.21 | 21.73 ± 9.72 | 99.5 | 378.2 |
| 42 | 0.53 ± 0.28 | 0.96 ± 0.51 | 99.0 | 493.0 |
| 47 | 89.23 ± 24.23 | 46.23 ± 2.34 | 98.2 | 436.1 |
| 60 | 5.32 ± 2.23 | 1.14 ± 0.34 | 96.5 | 448.9 |
| 61 | 77.65 ± 21.34 | 33.26 ± 2.12 | 99.0 | 384.1 |
| 73 | 135.4 ± 32.23 | 60.62 ± 3.28 | 98.9 | 386.0 |
| 77 | 32.24 ± 9.32 | 82.28 ± 19.34 | 99.2 | 429.1 |
| 86 | 98.32 ± 65.23 | 50.12 ± 1.34 | 95.5 | 414.1 |
| 94 | 0.28 ± 0.32 | 0.54 ± 0.23 | 96.0 | 498.8 |
| 96 | 0.72 ± .0.28 | 5.41 ± 2.29 | 98.7 | 334.0 |
| 99 | 54.54 ± 32.12 | 18.36 ± 1.34 | 99.5 | 457.9 |
| 108 | 56.79 ± 19.43 | 91.22 ± 33.2 | 98.8 | 299.8 |
| 116 | 210.21 ± 9.80 | 43.24 ± 13.67 | 97.3 | 421.0 |

Exemplary Embodiment 10

Patch-Clamp Electrophysiology Testing (1) Testing compound: compound number 21

(2) Testing method: Culture of ovary cell of Chinese hamster (CHO, Chinese Hamster Overy): steadily transfer the CHO cell culture of KCNQ2/Q3 channel into a composition containing 10% fetal bovine serum, 100 U/ml penicillin and DMEM culture solution of streptomycin, and allow digestion passage of trypsin. Spread the cell on a 12 mm round-shaped coverslip and culture on a 24-well cell culture plate.

Record membrane current using patch-clamp technique: The patch-clamp amplifier is HEKA-EPC10. The electrode solution uses amphotericin B (final concentration of 0.1~0.2 mg/ml) for perforated patch clamp recording. After polishing the microelectrodes, inject the electrode solution and control the to 2~4MΩ. The electrode solution used for recording CHO cell are (mM): KCl 160, HEPES 5, $MgCl_2$ 3, $CaCl_2$ 1, EGTA 2, with pH adjusted to 7.4 with KOH; Extracellular electrode composition are (mM): NaCl 160, KCl 2.5, HEPES 10, glucose 8, $MgCl_2$ 1, $CaCl_2$ 5. After the cell membrane and microelectrodes form a high resistance seal, clamp at −80 mV, wait 5-10 min and record the readings according to different activation procedures.

Figure 5:
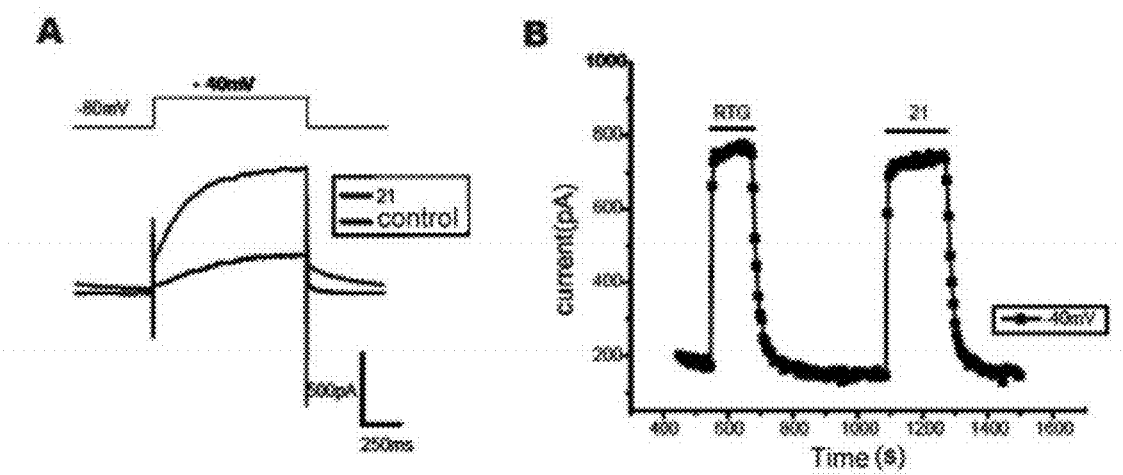
FIG. 5 is a graphical illustration of the compound activating KCNQ2/3 channel current according to the above preferred embodiment of the present invention.

(3) Testing results: Referring to FIG. 5, FIG. 5a is the current chart of compound number 21 in activating KCNQ2/3 channel in which the clamping voltage is −80 mV and is depolarized to −40 mV. It is shown that the channel current is activated and the compound number 21 can activate the KCNQ2/3 channel current significantly. For FIG. 5b, the current is depolarized to a level which is below −40 mV, the vertical axis is the plateau of activation current, the horizontal axis is the time of recording, and Retigabine (RTG) is used as control.

Since the compound of the present invention has an opening effect on KCNQ family potassium channel, it is believed that they can be used to promote the current in voltage-dependent potassium channel in mammals (such as human beings), and is suitable for treating KCNQ family potassium ion channel related diseases which are sensitive to current increase, such as epilepsy, different kinds of anxiety disorder and different kinds of neuropathic pain.

Exemplary Embodiment 11

"The maximum electric shock" experiment: The experiment uses electrical method to measure non-specific CNS-induced seizures.

Pharmaceutical composition used: the compound number 21 for the testing group, phenyloin for positive control group.

Experimental method: Apply corneal electrode in male mice of each group, apply 26 mA square wave current for 0.4 second, and forced feeding the pharmaceutical composition after inducing convulsion which is characterized by hindlimb tonic extension (Wlaz et al., Epilepsy Research 1998, 30, 219-229). Dosages for the testing group are: 10 mg/kg (body weight) per administration, 25 mg/kg (body weight) per administration, and 50 mg/kg (body weight) per administration respectively. For control group, dosage is 25 mg/kg (body weight) per administration.

Testing results: the compound of the present invention has an anticonvulsant effect, which is as significant as the effect of phenyloin, where $ED_{50}$=12.2±0.08 mg/kg.

Exemplary Embodiment 12

"Pilocarpine-Induced Seizures" Experiment

Pilocarpine-induced seizure is, in general, difficult to treat by using the existing anti-epileptic drug, so it belongs to "drug-resistance epilepsy" model.

Pharmaceutical composition used: the compound number 24 for the testing group, phenyloin for positive control group.

Experimental method: Inject 250 mg/kg pilocarpine into the male mice of each group by intraperitoneal injection, induce pilocarpine-induced seizure, observe walking abnormality caused by seizures activities in 30 minutes (Starr et al, Pharmacology Biochemistry and Behavior 1993, 45, 321-325). Apply intraperitoneal injection. Dosages for the testing group are: 1 mg/kg (body weight) per administration, 5 mg/kg (body weight) per administration, and 10 mg/kg (body weight) per administration respectively. For control group, dosage is 50 mg/kg (body weight) per administration.

Testing results: the compound of the present invention has an anti-epilepsy effect, which is more significant than the effect of phenyloin, where $ED_{50}$=5.1±0.05 mg/kg. Compared with the positive control group, the statistically significant difference is not significant, with p>0.05.

Exemplary Embodiment 13

"Amygdala Kindling" Experiment

This experiment is used to measure the disease progress, when further stimulation is applied, the seizure level of the animal in this model will be increased as in the situation of normal animal.

Pharmaceutical composition used: suspended solution of sodium carboxymethyl cellulose containing the compound number 21 for the testing group, suspended solution of sodium carboxymethyl cellulose for the positive control group, with concentration equal to the suspended solution of the testing group.

Testing method: perform surgery to implant tri-polar electrode into dorsolateral amygdale of rat. After surgery, allow the animal to recover, then administer testing compound or pharmaceutical solvent agent of different dosages to rat of different groups. The animal is treated with electrical stimulation at a value which is +25 μA of the initial discharge threshold on a daily basis for 3-5 weeks, and record each seizure incidence in which the level of seizure, the duration of the seizure, and electrical duration after discharge are recorded (Racine. Electroencephalography and Clinical Neurophysiology 1972, 32, 281-294). Dosage level is the same as that of exemplary embodiment 11.

Testing results: In the control group, the seizure level and the time period after discharge process of amygdala have no significant changes (p>0.05), while in the testing group, when compared to pre-administration of pharmaceutical compound, the increased in the seizure level and shorten time period after discharge process of amygdale show significant changes, which is statistically significant (p<0.01) when compared to the control group.

Exemplary Embodiment 14

Formalin-Induced Pain Model

Pharmaceutical composition used: the compound number 42 for the testing group, no medication for the positive control group, which is a blank control model.

Testing method: Male SD rats are randomly divided into control group, ipsilateral treatment group (treatment on the same side) and contralateral treatment group (treatment on the opposite side). After 30 minutes from administration of pharmaceutical compound, administer 20 μl of 20 g/L formalin by subcutaneous injection in foot bottom of back paw on the same side or the opposite side of pharmaceutical compound administration, an occurrence of typical lateral swinging and shaking of rat's tail is deemed as successful in preparing induced-pain model, in the next 60 minutes, observe the rat's licking and biting behavior towards the formalin's injection paw at each 5-min interval.

Testing results: the rat in the first phase after formalin injection (0-10 min), the accumulated time of licking/biting back paw of the treatment group and the control group has no significant difference (p>0.05). In the second phase (10-60 min), the ipsilateral treatment group of different dosages show a decrease in accumulated time of licking/biting back paw when compared to the control group, and the differences is statistically significant (p<0.05). Accordingly, the compound of the present invention has significant analgesic effect.

Exemplary Embodiment 15

Testing of Toxic Side Effect

Measure the side effect on central nervous system by measuring the time period of the rat staying in a rolling device (Capacio et al, Drug and Chemical toxicology 1992, 15, 177-201); or by recording the number of count of passing through the infrared light in the experimental cage so as to determine the voluntary activity level of rat (Watson et al., Neuropharmacology 1997, 36, 1369-1375). Measure the effect of the compound on low-temperature effect of core body temperature in animal with a rectal probe or a radiotelemetry transmitter for detecting body temperature.

Testing results show that there are almost no side effect or negligible side effect in clinical trial in the compound of the present invention.

Exemplary Embodiment 16

Manufacture into a tablet form according to the conventional method, wherein each tablet has the following ingredients:

compound number 21, 50 mg lactose, 70 mg magnesium stearate, 3 mg polyvinyl pyrrolidone, 130 mg Exemplary Embodiment 17

Manufacture into a capsule form according to the conventional method, wherein each capsule has the following ingredients:

compound number 35, 50 mg lactose, 70 mg corn starch, 25 mg magnesium stearate, 1 mg polyvinyl pyrrolidone, 130 mg The chemical structure of the compounds of the invention are illustrated: (see Table 3)

TABLE 3

| Compound No. | Structural formula |
|---|---|
| 1 | $F_3C$, $COOC_2H_5$ (pyrazolo-pyrimidinone with phenyl) |

TABLE 3-continued

| Compound No. | Structural formula |
|---|---|
| 2 | $F_3C$, with 3,4-dimethoxyphenyl and $CF_3$ substituent |
| 3 | $F_3C$, $COOC_2H_5$, $CH_2Cl$ |
| 4 | $F_3C$, $COOC_2H_5$, $CH_3$ |
| 5 | $F_3C$, $COOC_2H_5$, phenyl |
| 6 | $F_3C$, $COOC_2H_5$, dichlorofluoropyridyl |
| 7 | $F_3C$, $COOC_2H_5$, $CH_2$-N-piperidine |
| 8 | $F_3C$, with 4-fluorophenyl and 4-chlorophenyl substituents |

TABLE 3-continued
| Compound No. | Structural formula |
|---|---|
| 9 | 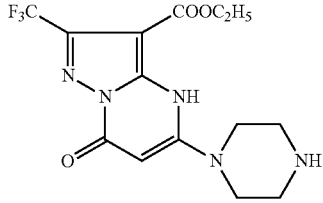 |
| 10 | 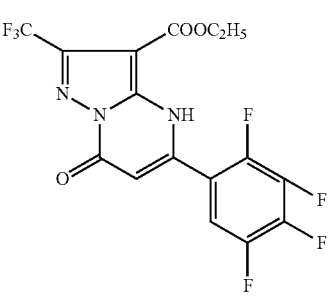 |
| 11 | 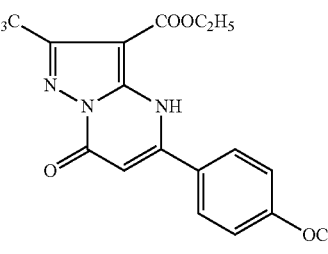 |
| 12 | 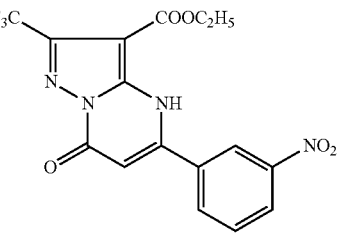 |
| 13 | 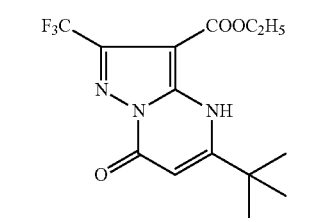 |
| 14 | 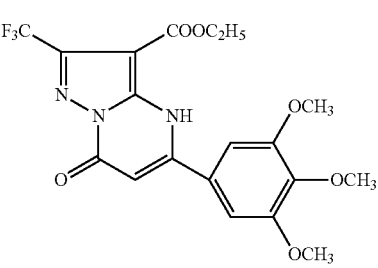 |
| 15 | 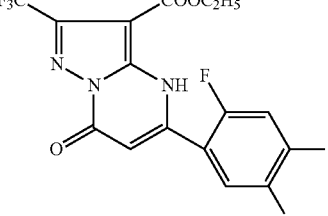 |
| 16 | 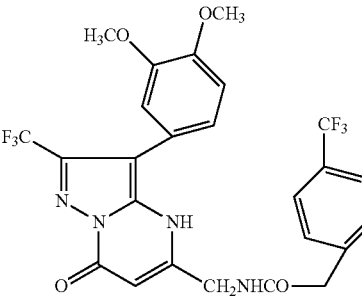 |
| 17 | 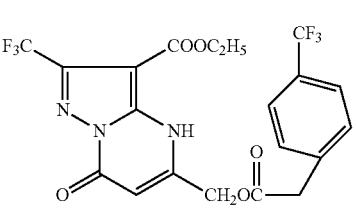 |
| 18 | 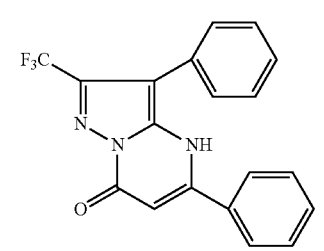 [SMILES: O=c1cc(-c2ccccc2)[nH]c2c(-c3ccccc3)c(C(F)(F)F)nn12] |
| 19 | |
| 20 | 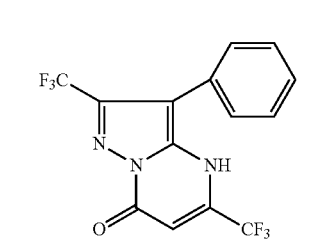 [SMILES: O=c1cc(C(F)(F)F)[nH]c2c(-c3ccccc3)c(C(F)(F)F)nn12] |

TABLE 3-continued

| Compound No. | Structural formula |
|---|---|
| 21 | 2-(trifluoromethyl)-3-phenyl-6-(chloromethyl)pyrazolo[1,5-a]pyrimidin-7(4H)-one |
| 22 | 2-(trifluoromethyl)-3-(4-fluorophenyl)-6-(2,6-dichloro-5-fluoropyridin-3-yl)pyrazolo[1,5-a]pyrimidin-7(4H)-one |
| 23 | 2-(trifluoromethyl)-3-(3,4-dimethoxyphenyl)-6-(2,6-dichloro-5-fluoropyridin-3-yl)pyrazolo[1,5-a]pyrimidin-7(4H)-one |
| 24 | 2-(trifluoromethyl)-3-phenyl-6-(2,6-dichloro-5-fluoropyridin-3-yl)pyrazolo[1,5-a]pyrimidin-7(4H)-one |
| 25 | 2-(trifluoromethyl)-3-(4-fluorophenyl)-6-(cyclohexylmethyl)pyrazolo[1,5-a]pyrimidin-7(4H)-one |
| 26 | 2-(trifluoromethyl)-3-phenyl-6-(4-chlorophenyl)pyrazolo[1,5-a]pyrimidin-7(4H)-one |
| 27 | 2-(trifluoromethyl)-3-phenyl-6-(piperazin-1-yl)pyrazolo[1,5-a]pyrimidin-7(4H)-one |
| 28 | 2-(trifluoromethyl)-3-phenyl-6-(2,3,4,5-tetrafluorophenyl)pyrazolo[1,5-a]pyrimidin-7(4H)-one |
| 29 | 2-(trifluoromethyl)-3-phenyl-6-(4-methoxyphenyl)pyrazolo[1,5-a]pyrimidin-7(4H)-one |
| 30 | 2-(trifluoromethyl)-3-phenyl-6-(3-nitrophenyl)pyrazolo[1,5-a]pyrimidin-7(4H)-one |

TABLE 3-continued

| Compound No. | Structural formula |
|---|---|
| 31 | (structure: 2-CF₃, 3-phenyl, 6-tert-butyl pyrazolo[1,5-a]pyrimidin-7(4H)-one) |
| 32 | (structure: 2-CF₃, 3-phenyl, 6-(3,4,5-trimethoxyphenyl) pyrazolo[1,5-a]pyrimidin-7(4H)-one) |
| 33 | (structure: 2-CF₃, 3-phenyl, 6-(2,4,5-trifluorophenyl) pyrazolo[1,5-a]pyrimidin-7(4H)-one) |
| 34 | (structure: 2-CF₃, 3-phenyl, 6-isopropyl pyrazolo[1,5-a]pyrimidin-7(4H)-one) |
| 35 | (structure: 2-CF₃, 3-phenyl, 6-CH₂NHCO-O-CH₂-(4-CF₃-phenyl) pyrazolo[1,5-a]pyrimidin-7(4H)-one) |
| 36 | (structure: 2-CF₃, 3-phenyl, 6-CH₂OC(O)CH₂-(4-CF₃-phenyl) pyrazolo[1,5-a]pyrimidin-7(4H)-one) |
| 37 | (structure: 2-CF₃, 3-(1-naphthyl), 6-phenyl pyrazolo[1,5-a]pyrimidin-7(4H)-one) |
| 38 | (structure: 2-CF₃, 3-(1-naphthyl), 6-CF₃ pyrazolo[1,5-a]pyrimidin-7(4H)-one) |
| 39 | (structure: 2-CF₃, 3-(1-naphthyl), 6-CH₂Cl pyrazolo[1,5-a]pyrimidin-7(4H)-one) |
| 40 | (structure: 2-CF₃, 3-(1-naphthyl), 6-CH₃ pyrazolo[1,5-a]pyrimidin-7(4H)-one) |
| 41 | (structure: 2-CF₃, 3-(1-naphthyl), 6-phenyl pyrazolo[1,5-a]pyrimidin-7(4H)-one) |

TABLE 3-continued

| Compound No. | Structural formula |
|---|---|
| 42 | |
| 43 | |
| 44 | |
| 45 | |
| 46 | |
| 47 | |
| 48 | |
| 49 | |
| 50 | |

TABLE 3-continued
| Compound No. | Structural formula |
|---|---|
| 51 | 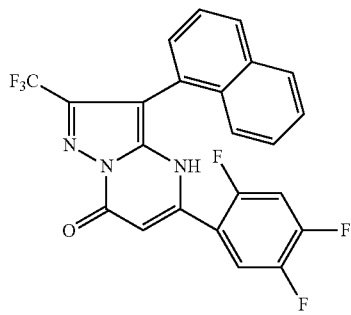 [SMILES: O=c1cc(-c2cc(F)c(F)cc2F)[nH]c2c(-c3cccc4ccccc34)c(C(F)(F)F)nn12] |
| 52 | 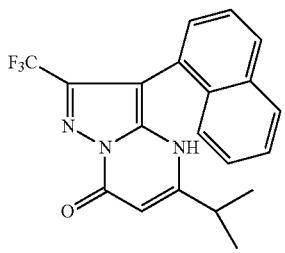 [SMILES: CC(C)c1cc(=O)n2nc(C(F)(F)F)c(-c3cccc4ccccc34)c2[nH]1] |
| 53 | 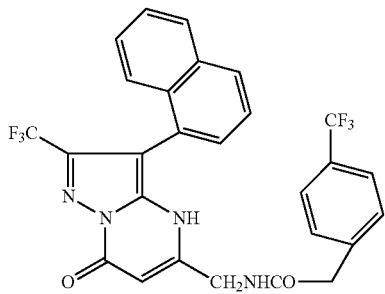 |
| 54 | 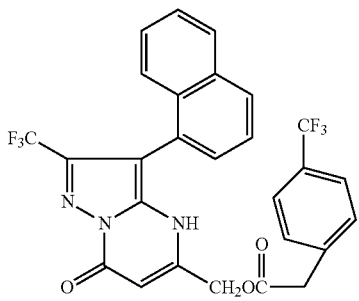 |
| 55 | 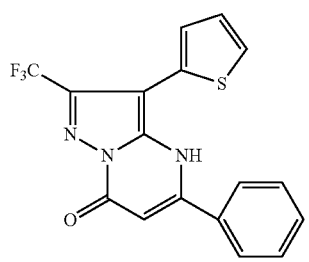 [SMILES: O=c1cc(-c2ccccc2)[nH]c2c(-c3cccs3)c(C(F)(F)F)nn12] |
TABLE 3-continued
| Compound No. | Structural formula |
|---|---|
| 56 | 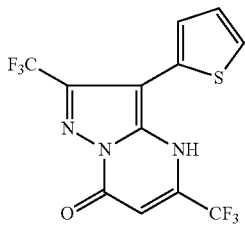 [SMILES: O=c1cc(C(F)(F)F)[nH]c2c(-c3cccs3)c(C(F)(F)F)nn12] |
| 57 | 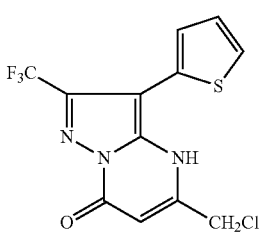 |
| 58 | 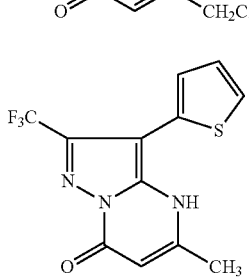 |
| 59 | 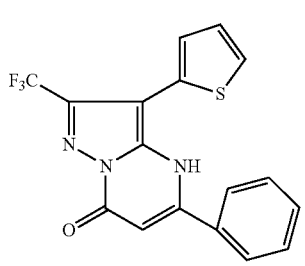 [SMILES: O=c1cc(-c2ccccc2)[nH]c2c(-c3cccs3)c(C(F)(F)F)nn12] |
| 60 | 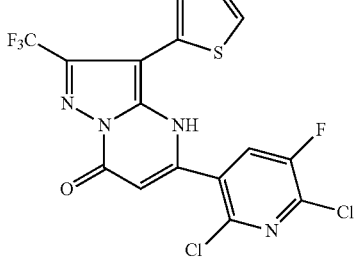 |
| 61 | 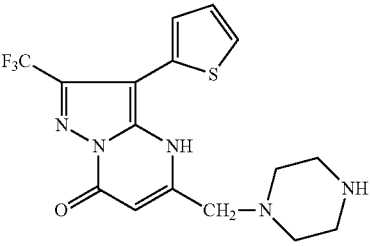 [SMILES: O=c1cc(CN2CCNCC2)[nH]c2c(-c3cccs3)c(C(F)(F)F)nn12] |

TABLE 3-continued
| Compound No. | Structural formula |
|---|---|
| 62 | 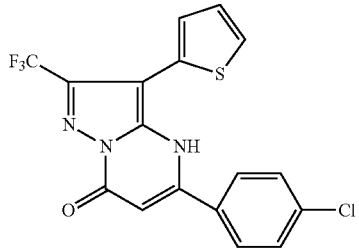 [SMILES: O=c1cc(-c2ccc(Cl)cc2)[nH]c2c(-c3cccs3)c(C(F)(F)F)nn12] |
| 63 | 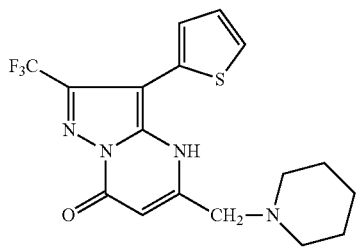 [SMILES: O=c1cc(CN2CCCCC2)[nH]c2c(-c3cccs3)c(C(F)(F)F)nn12] |
| 64 | 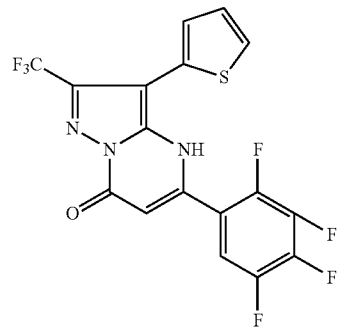 [SMILES: O=c1cc(-c2cc(F)c(F)c(F)c2F)[nH]c2c(-c3cccs3)c(C(F)(F)F)nn12] |
| 65 | 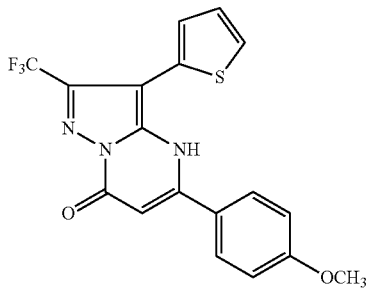 [SMILES: COc1ccc(-c2cc(=O)n3nc(C(F)(F)F)c(-c4cccs4)c3[nH]2)cc1] |
| 66 | 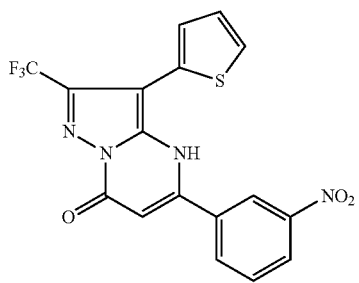 [SMILES: O=c1cc(-c2cccc([N+](=O)[O-])c2)[nH]c2c(-c3cccs3)c(C(F)(F)F)nn12] |
| 67 | 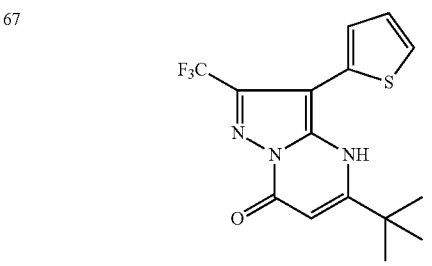 |
| 68 | 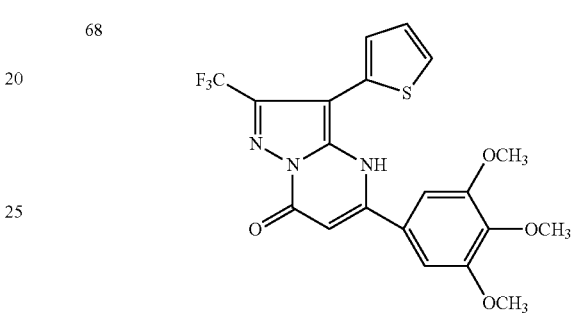 |
| 69 | 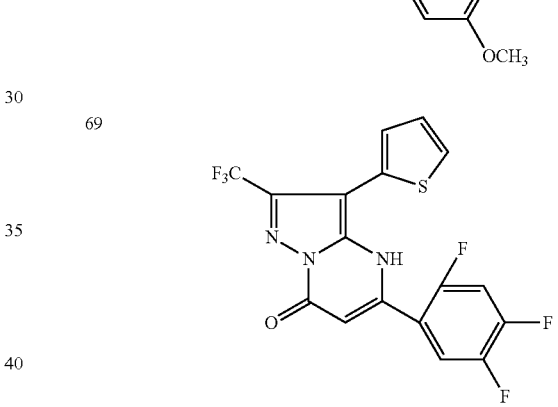 |
| 70 | 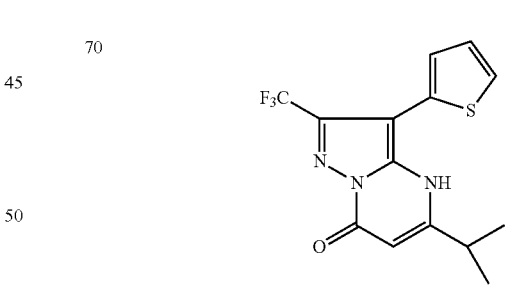 |
| 71 | 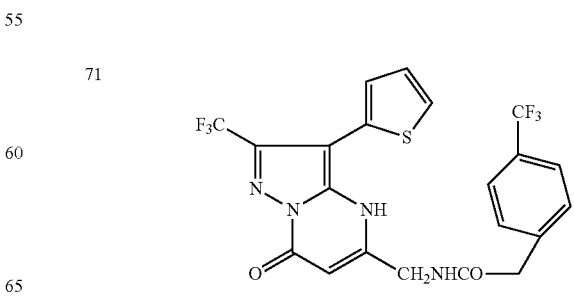 |

TABLE 3-continued

| Compound No. | Structural formula |
|---|---|
| 72 | (structure) |
| 73 | (structure) |
| 74 | (structure) |
| 75 | (structure) |
| 76 | (structure) |
| 77 | (structure) |
| 78 | (structure) |
| 79 | (structure) |
| 80 | (structure) |
| 81 | (structure) |
| 82 | (structure) |
| 83 | (structure) |

TABLE 3-continued

| Compound No. | Structural formula |
|---|---|
| 84 | 4-chlorophenyl and phenyl substituted pyrazolo[1,5-a]pyrimidin-7(4H)-one with CH₂OCOCF₃ |
| 85 | F₃C and phenyl substituted pyrazolo[1,5-a]pyrimidin-7(4H)-one with CH₂OCOCF₃ |
| 86 | F₃C and piperazinyl substituted pyrazolo[1,5-a]pyrimidin-7(4H)-one with CH₂OCOCF₃ |
| 87 | F₃C and 4-fluorophenyl substituted pyrazolo[1,5-a]pyrimidin-7(4H)-one with CH₂NHCOCF₃ |
| 88 | F₃C and thienyl substituted pyrazolo[1,5-a]pyrimidin-7(4H)-one with CH₂NHCOCF₃ |
| 89 | 4-chlorophenyl and thienyl substituted pyrazolo[1,5-a]pyrimidin-7(4H)-one with CH₂NHCOCF₃ |
| 90 | 4-chlorophenyl and thienyl substituted pyrazolo[1,5-a]pyrimidin-7(4H)-one with 5-fluoro-2,6-dichloropyridin-3-yl |
| 91 | 4-chlorophenyl and phenyl substituted pyrazolo[1,5-a]pyrimidin-7(4H)-one with 5-fluoro-2,6-dichloropyridin-3-yl |
| 92 | 4-chlorophenyl and naphthyl substituted pyrazolo[1,5-a]pyrimidin-7(4H)-one with 5-fluoro-2,6-dichloropyridin-3-yl |
| 93 | Cl₃C and naphthyl substituted pyrazolo[1,5-a]pyrimidin-7(4H)-one with 5-fluoro-2,6-dichloropyridin-3-yl |
| 94 | Cl₃C and thienyl substituted pyrazolo[1,5-a]pyrimidin-7(4H)-one with 5-fluoro-2,6-dichloropyridin-3-yl |

TABLE 3-continued
| Compound No. | Structural formula |
|---|---|
| 95 | 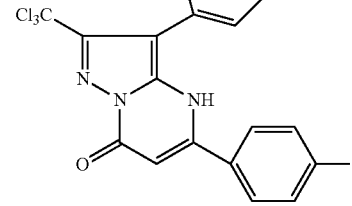 |
| 96 | |
| 97 | |
| 98 | |
| 99 | |
TABLE 3-continued
| Compound No. | Structural formula |
|---|---|
| 100 | 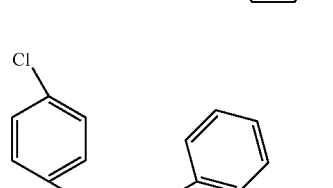 |
| 101 | |
| 102 | |
| 103 | |
| 104 | |

TABLE 3-continued

| Compound No. | Structural formula |
|---|---|
| 105 | (pyrazolo[1,5-a]pyrimidin-7(4H)-one with 3-phenyl and 5-CH₂-piperidinyl) |
| 106 | (2-methyl-3-(thiophen-2-yl)pyrazolo[1,5-a]pyrimidin-7(4H)-one with CH₂NHCO-(4-CF₃-phenyl)) |
| 107 | (2-methyl-3-(thiophen-2-yl)pyrazolo[1,5-a]pyrimidin-7(4H)-one with CH₂Cl) |
| 108 | (2-Cl-3-(thiophen-2-yl)pyrazolo[1,5-a]pyrimidin-7(4H)-one with CH₂Cl) |
| 109 | (2-Cl-3-phenylpyrazolo[1,5-a]pyrimidin-7(4H)-one with CH₂Cl) |
| 110 | (2-Cl-3-(naphthalen-1-yl)pyrazolo[1,5-a]pyrimidin-7(4H)-one with CH₂Cl) |
| 111 | (2-Cl-3-phenylpyrazolo[1,5-a]pyrimidin-7(4H)-one with CH₂-piperidinyl) |
| 112 | (2-Cl-3-phenylpyrazolo[1,5-a]pyrimidin-7(4H)-one with CF₃) |
| 113 | (2-Cl-3-(thiophen-2-yl)pyrazolo[1,5-a]pyrimidin-7(4H)-one with CH₂NHCO-(4-CF₃-phenyl)) |
| 114 | (2-Cl-3-(thiophen-2-yl)pyrazolo[1,5-a]pyrimidin-7(4H)-one with CH₂Cl) |
| 115 | (2-Cl-3-phenylpyrazolo[1,5-a]pyrimidin-7(4H)-one with CH₂COCH₃) |
| 116 | (2-Cl-3-(naphthalen-2-yl)pyrazolo[1,5-a]pyrimidin-7(4H)-one with CH₂NHCOCF₃) |
| 117 | (2-Cl-3-phenylpyrazolo[1,5-a]pyrimidin-7(4H)-one with COOCF₃) |

TABLE 3-continued

| Compound No. | Structural formula |
|---|---|
| 118 | 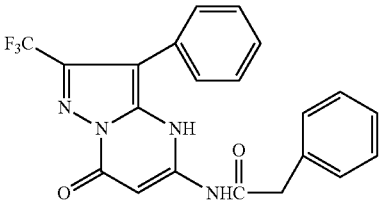 |
| 119 | 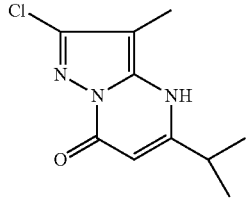 |
| 120 | 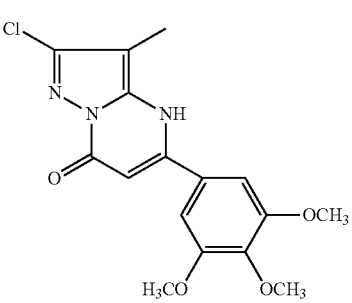 [SMILES: COc1cc(-c2cc(=O)n3nc(Cl)c(C)c3[nH]2)cc(OC)c1OC] |

In the present invention, the compound having the same compound number are the same compound (for example, the compound number 21 in table 1, table 2, table 3 and exemplary embodiment 2 are the same compound) which is described in different approaches.

The above exemplary embodiment, experimental exemplary embodiment and pharmaceutical exemplary embodiment are used to further describe the present invention, but not limiting in any forms.

One skilled in the art will understand that the embodiment of the present invention as shown in the drawings and described above is exemplary only and not intended to be limiting.

It will thus be seen that the objects of the present invention have been fully and effectively accomplished. It embodiments have been shown and described for the purposes of illustrating the functional and structural principles of the present invention and is subject to change without departure from such principles. Therefore, this invention includes all modifications encompassed within the spirit and scope of the following claims.

What is claimed is:

1. A compound having a general formula of:

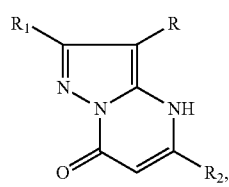

where
R is methyl acetate substituent;
$R_1$ is tri-halogenated alkyl;
$R_2$ is one of phenyl and substituted phenyl.

2. A compound having a general formula of:

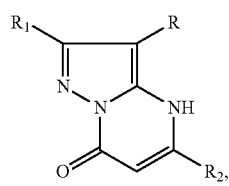

wherein said R, $R_1$, $R_2$ are selected from the group consisting of:
(i) wherein said R is one of naphthalenyl and substituted naphthalenyl, said $R_1$ is tri-halogenated alkyl, and said $R_2$ is phenyl or substituted phenyl;
(ii) wherein said $R_1$ is halogenated alkyl, said R is thiophenyl and said $R_2$ is one of phenyl and substituted phenyl;
(iii) wherein said $R_1$ is halogenated alkyl, said R is thiophenyl and said $R_2$ is one of alkyl and substituted alkyl;
(iv) wherein said R is one of naphthalenyl and substituted naphthalenyl, said $R_1$ is tri-halogenated alkyl, and said $R_2$ is one of phenyl and substituted phenyl;
(v) wherein said R is thiophenyl, said $R_1$ is selected from halogenated alkyl and alkylated halide, and said $R_2$ is

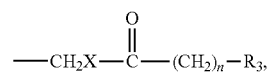

wherein X is one of O and NH, and n is a natural number selected from 0 to 6, wherein $R_3$ is selected from the group consisting of: hydrogen, halogen, aryl, and substituted aryl; and
(vi) wherein said $R_1$ is halogenated alkyl, said R is thiophenyl and said $R_2$ is one of pyridine and a substituted pyridine.

3. A compound having a general formula of:

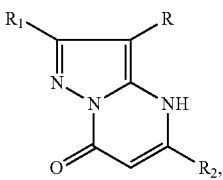

2-trifluoromethyl-3-phenyl-5-chloromethylpyrazole[1,5-a]pyrimidin-7(4H)-one;
2-trifluoromethyl-3-phenyl-5-(2,6-dichloro-5-fluoropyrimidin-3-yl)pyrazole[1,5-a]pyrimidin-7(4H)-one;
2-trifluoromethyl-3-(naphthalen-1-yl)-5-chloromethylpyrazole[1,5]pyrimidin-7(4H)-one;
3-(naphthalen-1-yl)-2,5-bis(trifluoromethyl)pyrazole[1,5]pyrimidin-7(4H)-one;
2-trifluoromethyl-3-phenyl-5-(piperidin-1-ylmethyl)pyrazole pyrimindin-7(4H)-one; and
N-((2-trifluoromethyl-3-phenyl-7-oxy-4,7-dihydropyrazole[1,5-a]pyrimidin-5-yl)-2-(4-trifluoromethylphenyl)acetamide.

* * * * *